(12) United States Patent
Hu et al.

(10) Patent No.: US 12,103,978 B2
(45) Date of Patent: Oct. 1, 2024

(54) METHODS AND MATERIALS FOR TREATING CANCER

(71) Applicant: SHANGHAI MIRACOGEN INC., Shanghai (CN)

(72) Inventors: Chaohong Hu, Shanghai (CN); Hu Li, Shanghai (CN); Wenchao Liu, Shanghai (CN); Zhenyu Dai, Shanghai (CN)

(73) Assignee: SHANGHAI MIRACOGEN INC., Shanghai (CN)

( * ) Notice: Subject to any disclaimer, the term of this patent is extended or adjusted under 35 U.S.C. 154(b) by 663 days.

(21) Appl. No.: 16/763,335

(22) PCT Filed: Jun. 15, 2018

(86) PCT No.: PCT/CN2018/091444
§ 371 (c)(1),
(2) Date: May 12, 2020

(87) PCT Pub. No.: WO2019/237322
PCT Pub. Date: Dec. 19, 2019

(65) Prior Publication Data
US 2021/0087292 A1 Mar. 25, 2021

(51) Int. Cl.
| | |
|---|---|
| *C07K 16/32* | (2006.01) |
| *A61K 39/00* | (2006.01) |
| *A61K 39/395* | (2006.01) |
| *A61K 47/68* | (2017.01) |
| *A61P 35/00* | (2006.01) |
| *C07K 16/28* | (2006.01) |

(52) U.S. Cl.
CPC ........ *C07K 16/32* (2013.01); *A61K 39/39541* (2013.01); *A61K 47/6803* (2017.08); *A61K 47/6851* (2017.08); *A61K 47/6855* (2017.08); *A61K 47/6889* (2017.08); *A61P 35/00* (2018.01); *C07K 16/2818* (2013.01); *C07K 16/2827* (2013.01); *A61K 2039/507* (2013.01); *C07K 2317/24* (2013.01); *C07K 2317/41* (2013.01); *C07K 2317/732* (2013.01); *C07K 2317/734* (2013.01); *C07K 2317/92* (2013.01)

(58) Field of Classification Search
CPC ............ A61K 47/6851; A61K 47/6803; A61K 47/68031; A61K 47/6889; C07K 2317/92; C07K 231/41; C07K 2317/41
See application file for complete search history.

(56) References Cited

U.S. PATENT DOCUMENTS 9,880,176 B2 * 1/2018 Jaga ................... G01N 33/6854

FOREIGN PATENT DOCUMENTS

| CA | 2 900 912 A1 | 8/2014 | |
|---|---|---|---|
| CA | 2 916 202 A1 | 12/2014 | |
| CN | 103394083 A | 11/2013 | |
| CN | 105308071 A | 2/2016 | |
| CN | 106999606 B | 6/2020 | |
| WO | WO-2005081711 A2 * | 9/2005 | ............. A61K 38/08 |
| WO | WO-2014013019 A1 * | 1/2014 | ....... A61K 39/39533 |
| WO | 2014/065661 A1 | 5/2014 | |
| WO | 2014/145159 A2 | 9/2014 | |

OTHER PUBLICATIONS

Muntasell et al (Frontiers in Immunology, 2017, vol. 8, Article 1544, 10 pages (Year: 2017).*
Iwata et al (Molecular Cancer therapeutics, ePub Apr. 27, 2018, vol. 17, pp. 1494-1503) (Year: 2018).*
Muller et al (Science Translational Medicine, 2015, vol. 7, pp. 315ra188, 14 pages). (Year: 2015).*
Louie et al (Biotechnology and Bioengineering, 2016, vol. 114, pp. 632-644). (Year: 2016).*
Kim et al (mAbs, 2017, vol. 9, pp. 704-714) (Year: 2017).*
Perez et al (Drug discovery Today, 2014, vol. 19, pp. 869-881), (Year: 2014).*
Hamblett ('Her2-Targeted ADCs: At the Forefront of ADC Technology Development', In "Innovations for Next-Generation Antibody-Drug Conjugates", pp. 163-185, M. Damelin, Ed., Humana Press, available on-line May 30, 2018) (Year: 2018).*
Dorion-Thibaudeau et al (Journal of Immunological Methods, 2014, vol. 408, pp. 24-34) (Year: 2014).*
Menderes et al (Clinical Cancer Research, 2017, vol. 23, pp. 5836-5845) (Year: 2017).*
Thomann et al., "Fc-galactosylation modulates antibody-dependent cellular cytotoxicity of therapeutic antibodies," *Molecular Immunology* 73:69-75 (2016).
Donaghy, "Effects of antibody, drug and linker on the preclinical and clinical toxicities of antibody-drug conjugates," *MABS* 8(4):659-671 (2016).
Konno et al., "Fucose content of monoclonal antibodies can be controlled by culture medium osmolality for high antibody-dependent cellular cytotoxicity," *Cytotechnology* 64:249-265 (2012).

(Continued)

*Primary Examiner* — Karen A. Canella
(74) *Attorney, Agent, or Firm* — Seed IP Law Group LLP

(57) ABSTRACT

This document provides methods and materials for treating a mammal having HER2-expressing cancers. For example, antibody drug conjugates containing an anti-HER2 antibody and at least one molecule of an anti-cancer drug are provided, as well as methods of administering such antibody drug conjugates to a mammal (e.g., a human) having a HER2-expressing cancer to treat the mammal.

20 Claims, 15 Drawing Sheets
Specification includes a Sequence Listing.

(56) References Cited

OTHER PUBLICATIONS

Yamane-Ohnuki et al., "Production of therapeutic antibodies with controlled fucosylation," *mAbs* 1(3):230-236 (May/Jun. 2009).

Li et al., "Preclinical evaluation of MRG002, a novel HER2-targeting antibody-drug conjugate with potent antitumor activity against HER2-positive solid tumors," *Antibody Therapeutics* 4(3):175-184 (2021).

\* cited by examiner

SEQUENCE LISTING

```
<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: MAB802 light chain CDR1

<400> SEQUENCE: 1

Ala Ser Gln Asp Val Asn Thr Ala Val Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: MAB802 light chain CDR2

<400> SEQUENCE: 2

Ser Ala Ser Phe Leu Tyr Ser
1               5

<210> SEQ ID NO 3
<211> LENGTH: 9
<212> TYPE: PRT
<213> ORGANISM: Artificial Sequence
<220> FEATURE:
<223> OTHER INFORMATION: MAB802 light chain CDR3

<400> SEQUENCE: 3

Gln Gln His Tyr Thr Thr Pro Pro Thr
1               5
```

```
<210> SEQ ID NO 4
<211> LENGTH: 214
<212> TYPE: PRT
<213> ORGANISM: Artificial Sequence
<220> FEATURE:
<223> OTHER INFORMATION: MAB802 light chain

<400> SEQUENCE: 4
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 5
<211> LENGTH: 10
<212> TYPE: PRT
<213> ORGANISM: Artificial Sequence
<220> FEATURE:
<223> OTHER INFORMATION: MAB802 heavy chain CDR1

<400> SEQUENCE: 5
```

Gly Phe Asn Ile Lys Asp Thr Tyr Ile His
1               5                   10

```
<210> SEQ ID NO 6
<211> LENGTH: 15
<212> TYPE: PRT
<213> ORGANISM: Artificial Sequence
<220> FEATURE:
<223> OTHER INFORMATION: MAB802 heavy chain CDR2

<400> SEQUENCE: 6
```

Ile Tyr Pro Thr Asn Gly Tyr Thr Arg Tyr Ala Asp Ser Val Lys
1               5                   10                  15

```
<210> SEQ ID NO 7
<211> LENGTH: 11
<212> TYPE: PRT
<213> ORGANISM: Artificial Sequence
<220> FEATURE:
<223> OTHER INFORMATION: MAB802 heavy chain CDR3

<400> SEQUENCE: 7

Trp Gly Gly Asp Gly Phe Tyr Ala Met Asp Tyr
1               5                   10

<210> SEQ ID NO 8
<211> LENGTH: 220
<212> TYPE: PRT
<213> ORGANISM: Artificial Sequence
<220> FEATURE:
<223> OTHER INFORMATION: MAB802 heavy chain fragment

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro
    210                 215                 220

<210> SEQ ID NO 9
<211> LENGTH: 450
<212> TYPE: PRT
<213> ORGANISM: Artificial Sequence
<220> FEATURE:
<223> OTHER INFORMATION: MAB802 heavy chain

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
```

```
            20                  25                  30
Tyr Ile His Trp Val Arg Gln Ala Pro Gly Lys Gly Leu Glu Trp Val
            35                  40                  45
Ala Arg Ile Tyr Pro Thr Asn Gly Tyr Thr Arg Tyr Ala Asp Ser Val
            50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
            210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
```

Gly Lys
    450

<210> SEQ ID NO 10
<211> LENGTH: 451
<212> TYPE: PRT
<213> ORGANISM: Artificial Sequence
<220> FEATURE:
<223> OTHER INFORMATION: MAB802 heavy chain variant

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

```
Tyr Thr Leu Pro Pro Ser Arg Asp Glu Leu Thr Lys Asn Gln Val Ser
    355             360             365

Leu Thr Cys Leu Val Lys Gly Phe Tyr Pro Ser Asp Ile Ala Val Glu
    370             375             380

Trp Glu Ser Asn Gly Gln Pro Glu Asn Asn Tyr Lys Thr Thr Pro Pro
385             390             395             400

Val Leu Asp Ser Asp Gly Ser Phe Phe Leu Tyr Ser Lys Leu Thr Val
            405             410             415

Asp Lys Ser Arg Trp Gln Gln Gly Asn Val Phe Ser Cys Ser Val Met
            420             425             430

His Glu Ala Leu His Asn His Tyr Thr Gln Lys Ser Leu Ser Leu Ser
        435             440             445

Pro Gly Lys
    450
```

METHODS AND MATERIALS FOR TREATING CANCER

STATEMENT REGARDING SEQUENCE LISTING

The Sequence Listing associated with this application is provided in text format in lieu of a paper copy, and is hereby incorporated by reference into the specification. The name of the text file containing the Sequence Listing is 850231_404USPC_SEQUENCE_LISTING.txt. The text file is 13 KB, was created on May 6, 2020, and is being submitted electronically via EFS-Web.

TECHNICAL FIELD

This document relates to methods and materials for treating a mammal having HER2-expressing cancers. For example, an antibody drug conjugate (ADC) containing an anti-HER2 antibody and at least one anti-cancer drug can be administered to a mammal (e.g., a human) having a HER2-expressing cancer to treat the mammal.

BACKGROUND

HER2 is a proto-oncogene of many cancers, especially breast and gastric cancers showing HER2 protein overexpression or gene amplification (Yan et al., 2014 *Cancer treatment reviews*, 40(6):770-780). About 15-20% of breast cancer patients overexpress HER2. This overexpression is closely related to increased malignancy and poor prognosis (Witton et al., 2003 *The Journal of pathology*, 200(3):290-297). Gastric cancer is the fifth most common cancer worldwide, with nearly one million new cases reported in 2012 (Ferlay et al., 2015 *International journal of cancer*, 136(5): E359-86). Approximately 20% of gastric cancers overexpress HER2 (American Cancer Society, 2017 "Targeted Therapies for Stomach Cancer," available online at cancer.org). HER2-expressing gastric cancer is an area of unmet medical need owing to genetic complexity and heterogeneity of the disease (Lordick et al., 2014 *Cancer treatment reviews*, 40(6):692-700).

Uses for current Food and Drug Administration (FDA) approved HER2-targeted therapies are limited. Trastuzumab (HERCEPTIN®) is FDA approved for treating HER2 positive metastatic breast cancer in combination with chemotherapy or taxol, and for the treatment of HER2-positive progress gastric cancers in combination with chemotherapy can remarkably prolong the survival of progressive gastric cancer patients (Van Cutsem et al., 2009 *J clin oncol*, 27:15s). PERJETA® (pertuzumab) is FDA approved for treating HER2-positive metastatic breast cancer patients who have not received prior anti-HER2 therapy or chemotherapy for metastatic disease in combination with trastuzumab and docetaxel. Kadcyla® (ado-trastuzumab emtansine; also referred to as T-DM1) is an FDA approved ADC containing trastuzumab linked to the cytotoxic agent emtansine for treating HER2 positive metastatic breast cancer patients who previously received trastuzumab and a taxane. Although the combination therapy can prolong overall survival of gastric cancer patients, half of them progress one year after treatment, the combination with trastuzumab only increased the response rate by approximately 12%, indicating resistance to trastuzumab among patients (Bang et al., 2010 *The Lancet*, 376(9742):687-697). Thus, there is a need for therapeutic agents targeting HER2 expressing cancers with increased efficacy relative to currently available HER2-targeted therapy options, and for therapeutic agents targeting HER2 expressing cancers are resistant to (e.g., that do not respond to; such as HER2 expressing cancers that relapse after treatment) currently available HER2-targeted therapy options.

SUMMARY

This document provides ADCs containing an antibody targeting a tumor-associated antigen (e.g., a HER2 polypeptide) and an anti-cancer drug that can be administered to a mammal (e.g., a human) having a cancer expressing the antigen (e.g., a HER2-expressing cancer) to treat the mammal. For example, an antibody drug conjugate (ADC) can include an anti-HER2 antibody (e.g., MAB802) and at least one molecule of an anti-cancer drug (e.g., an auristatin derivative such as monomethyl auristatin E (MMAE)) conjugated to the antibody. The ADC can include more than one molecule of an anti-cancer drug per antibody. In some cases, an ADC described herein can include an anti-HER2 antibody having increased levels of fucosylation (e.g., relative to other anti-HER2 antibodies). In some cases, an ADC described herein can include an increased drug/antibody ratio (DAR; e.g., relative to other ADCs containing anti-HER2 antibodies). This document also provides methods and materials for making and using ADCs containing an anti-HER2 antibody (e.g., MAB802) and one or more anti-cancer drugs (e.g., MMAE). For example, an ADC containing an anti-HER2 antibody and one or more anti-cancer drugs can be administered to a mammal (e.g., a human) having a HER2-expressing cancer to treat the mammal.

As demonstrated herein, the ADC MRG002, including a MAB802 antibody conjugated to MMAE via a vcLinker, exhibits anti-tumor activity in vitro and in vivo in HER2-expressing tumors. For example, MRG002 was markedly more potent than T-DM1 in inhibiting cancer cell growth in vitro in a number of breast and gastric cancer cells (Table 5). For example, MRG002 significantly inhibited in vivo tumor growth of breast cancers and gastric cancers, including in trastuzumab resistant tumors and T-DM1 resistant PDX models. Thus, MRG002 can address unmet medical needs for treating patients having HER2-expressing cancers, especially refractory HER2-expressing cancers (e.g., refractory HER2-expressing breast cancers and refractory HER2-expressing gastric cancers) and/or relapsed (e.g., metastatic) HER2-expressing cancers (e.g., relapsed HER2-expressing breast cancers and relapsed HER2-expressing gastric cancers).

In general, one aspect of this document features an ADC including an anti-HER2 antibody having greater than about 90% fucosylation, at least one molecule of an anti-cancer drug, and a linker connecting the anti-HER2 antibody and the molecule(s) of said anti-cancer drug.

The anti-HER2 antibody can be an IgG antibody. The anti-HER2 antibody can be a humanized antibody. The anti-HER2 antibody can include a light chain having the amino acid sequence set forth in SEQ ID NO:4. The anti-HER2 antibody can include a heavy chain having the amino acid sequence set forth in SEQ ID NO:8 (e.g., a heavy chain having the amino acid sequence set forth in SEQ ID NO:9). The anti-HER2 antibody can be a MAB802 antibody. The anti-HER2 antibody can have less than about 14% afucosylation. The anti-HER2 antibody can have a binding affinity for CD16 having an equilibrium dissociation constant (KD) value of greater than about $2.5 \times 10^{-08}$ M. The CD16 can be a human 176Val CD16a, and the KD can be from about $6.9 \times 10^{-08}$ M to about $7.1 \times 10^{-08}$ M. The CD16 can be a human 176Phe CD16a, and the KD can be from about $6.6 \times 10^{-07}$ M to about $6.9 \times 10^{-07}$ M. The ADC comprises at least three molecules of said anti-cancer drug per molecule of antibody. The anti-cancer drug can be an auristatin derivative (e.g., monomethyl auristatin E). The linker can be a cleavable linker (e.g., a valine citruline dipeptide linker).

In another aspect, this document features a composition including a plurality of ADCs, where the ADCs include an anti-HER2 antibody having greater than about 90% fucosylation, at least one molecule of an anti-cancer drug, and a linker connecting the anti-HER2 antibody and the molecule(s) of the anti-cancer drug. The anti-HER2 antibody can be an IgG antibody. The anti-HER2 antibody can be a humanized antibody. The anti-HER2 antibody can include a light chain having the amino acid sequence set forth in SEQ ID NO:4. The anti-HER2 antibody can include a heavy chain having the amino acid sequence set forth in SEQ ID NO:8 (e.g., a heavy chain having the amino acid sequence set forth in SEQ ID NO:9). The anti-HER2 antibody can be a MAB802 antibody. The anti-HER2 antibody can have less than about 14% afucosylation. The composition can have a drug/antibody ratio of greater than about 3.5 molecules of anti-cancer drug per anti-HER2 antibody (e.g., a drug/antibody ratio of about 3.8 molecules of anti-cancer drug per anti-HER2 antibody). The anti-cancer drug can be an auristatin derivative (e.g., monomethyl auristatin E). The linker can be a cleavable linker (e.g., a valine citruline dipeptide linker).

In another aspect, this document features a method for treating a mammal having a HER2-expressing cancer. The methods can include, or consist essentially of, administering an ADC to the mammal, where the ADC includes an anti-HER2 antibody having greater than about 90% fucosylation, at least one molecule of an anti-cancer drug, and a linker connecting the anti-HER2 antibody and the molecule(s) of anti-cancer drug. The mammal can be a human. The HER2-expressing cancer can be a breast cancer. The HER2-expressing cancer can be a gastric cancer. The HER2-expressing cancer can be a refractory cancer (e.g., a trastuzumab resistant cancer or a T-DM1 resistant cancer). The anti-HER2 antibody can be an IgG antibody. The anti-HER2 antibody can be a humanized antibody. The anti-HER2 antibody can include a light chain having the amino acid sequence set forth in SEQ ID NO:4. The anti-HER2 antibody can include a heavy chain having the amino acid sequence set forth in SEQ ID NO:8 (e.g., a heavy chain having the amino acid sequence set forth in SEQ ID NO:9). The anti-HER2 antibody can be a MAB802 antibody. The anti-HER2 antibody can have less than about 14% afucosylation. The anti-HER2 antibody can have a binding affinity for CD16 having a KD value of greater than about $2.5 \times 10^{-08}$ M. The CD16 can be a human 176Val CD16a, and the KD can be from about $6.9 \times 10^{-08}$ M to about $7.1 \times 10^{-08}$ M. The CD16 can be a human 176Phe CD16a, and the KD can be from about $6.6 \times 10^{-07}$ M to about $6.9 \times 10^{-07}$ M. The ADC can have antibody-dependent cellular cytotoxicity (ADCC) activity leading to from about 0% to about 30% cell lysis (e.g., from about 13.9% to about 15.7% cell lysis). The ADC can include at least three molecules of anti-cancer drug per molecule of anti-HER2 antibody. The anti-cancer drug can be an auristatin derivative (e.g., monomethyl auristatin E). The linker can be a cleavable linker (e.g., a valine citruline dipeptide linker). The administering can include administering about 0.6 mg to about 4 mg of ADC per kg body weight of the mammal.

Unless otherwise defined, all technical and scientific terms used herein have the same meaning as commonly understood by one of ordinary skill in the art to which this invention pertains. For example, the terms "e.g." and "such as," and grammatical equivalents thereof, the phrase "and without limitation" is understood to follow unless explicitly stated otherwise. For example, the singular forms "a," "an," and "the" include plural referents unless the context clearly dictates otherwise. For example, the term "about" means "approximately" (e.g., plus or minus approximately 10% of the indicated value). Although methods and materials similar or equivalent to those described herein can be used to practice the invention, suitable methods and materials are described below. It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

All of the tumor-bearing mice in the vehicle (ADC-2 solvent) group had been euthanized before Day 84 for compliance with the animal welfare requirements (4 mice had >20% reduction in body weight, and the other 7 mice had a tumor volume of over 2000 mm$^3$), therefore no picture of the tumors was taken.

Figure 9:
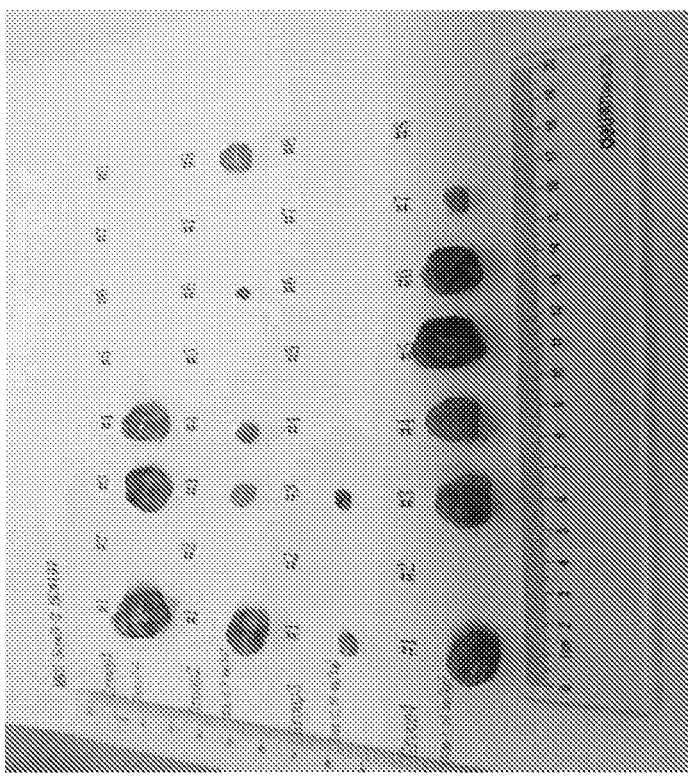
Figure 9:
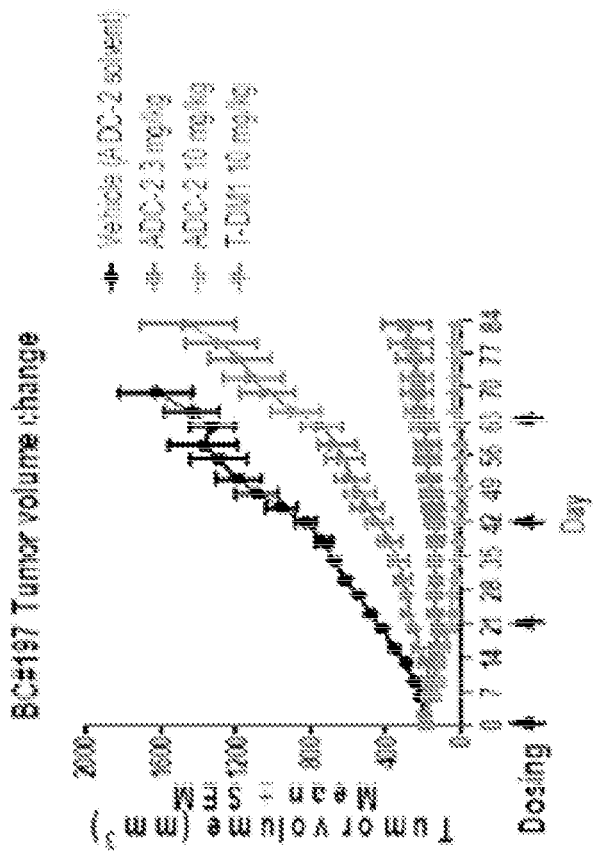

FIG. 9 shows the effect of MRG002 (ADC-2) and T-DM1 on the tumor volume of breast cancer PDX model BC #197 (left) and the photo of tumors at the end of the study (right). Group 1 is vehicle (ADC-2 solvent), Group 2 is ADC-2 at a dose of 3 mg/kg, Group 3 is ADC-2 at a dose of 10 mg/kg, and Group 4 is T-DM1 at a dose of 10 mg/kg. Five tumor-bearing mice in the ADC-2 solvent group had been euthanized before Day 84 for compliance with the animal welfare requirements (No. 8 mouse had >20% reduction in body weight, and No. 2, 5, 6 and 7 mice had a tumor volume of over 2000 mm$^3$), therefore no picture of their corresponding tumors was taken.

Figure 10:
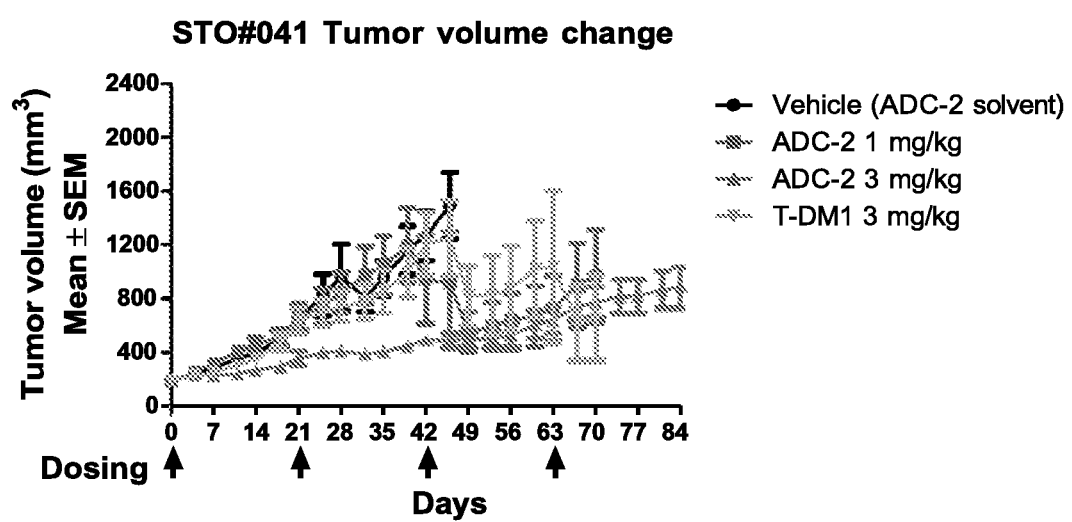

FIG. 10 shows the effect of MRG002 (ADC-2) and T-DM1 on the tumor volume of gastric cancer PDX model STO #041. All of the tumor-bearing mice in the vehicle (ADC-2 solvent) group had been euthanized before Day 84 for compliance with the animal welfare requirements (tumor volume exceeded 2000 mm$^3$).

Figure 11:
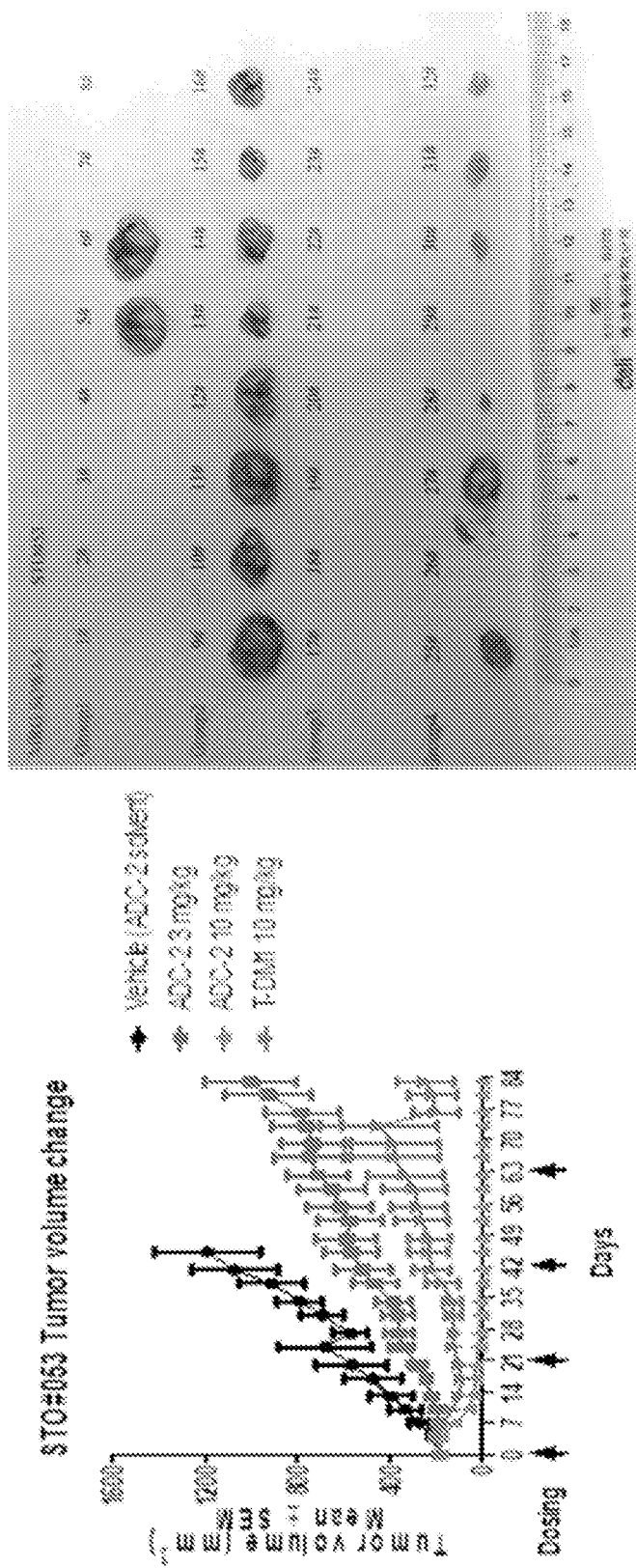

FIG. 11 shows the effect of MRG002 (ADC-2) and T-DM1 on the tumor volume of gastric cancer PDX model STO#053 (left) and the photo of tumors at the end of the study (right). Group 1 is vehicle (ADC-2 solvent), Group 2 is ADC-2 at a dose of 3 mg/kg, Group 3 is ADC-2 at a dose of 10 mg/kg, and Group 4 is T-DM1 at a dose of 10 mg/kg. Six tumor-bearing mice in the ADC-2 solvent group had been euthanized before Day 84 for compliance with the animal welfare requirements (No. 1, 2, 3, 4, 7 and 8 mice had tumor volume >2000 mm$^3$), therefore no picture of these tumors was taken.

Figure 12:
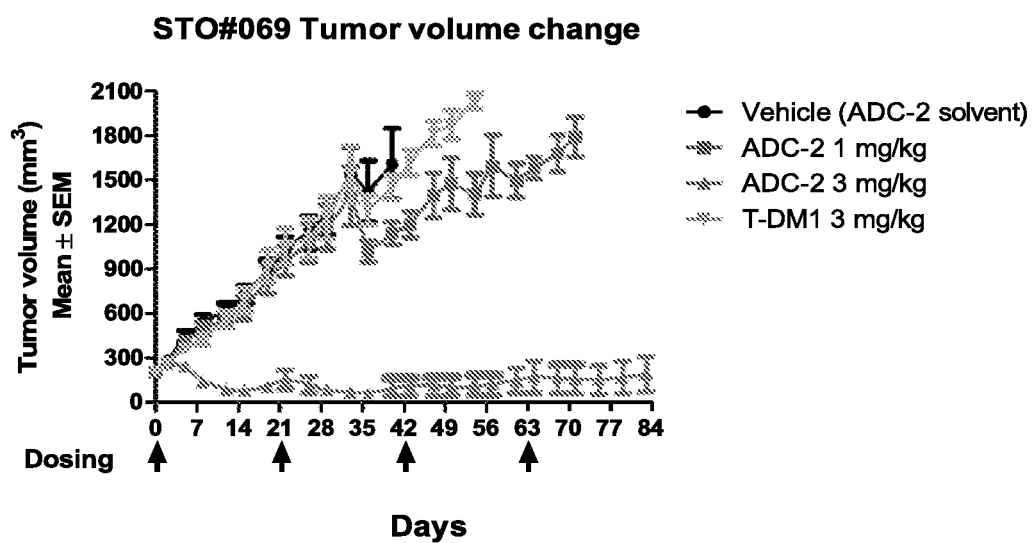

FIG. 12 shows the effect of MRG002 (ADC-2) and T-DM1 on the tumor volume of gastric cancer PDX model STO#069. All of the tumor-bearing mice in the vehicle (ADC-2 solvent) group had been euthanized before Day 84 for compliance with the animal welfare requirements (tumor volume exceeded 2000 mm$^3$).

Figure 13:
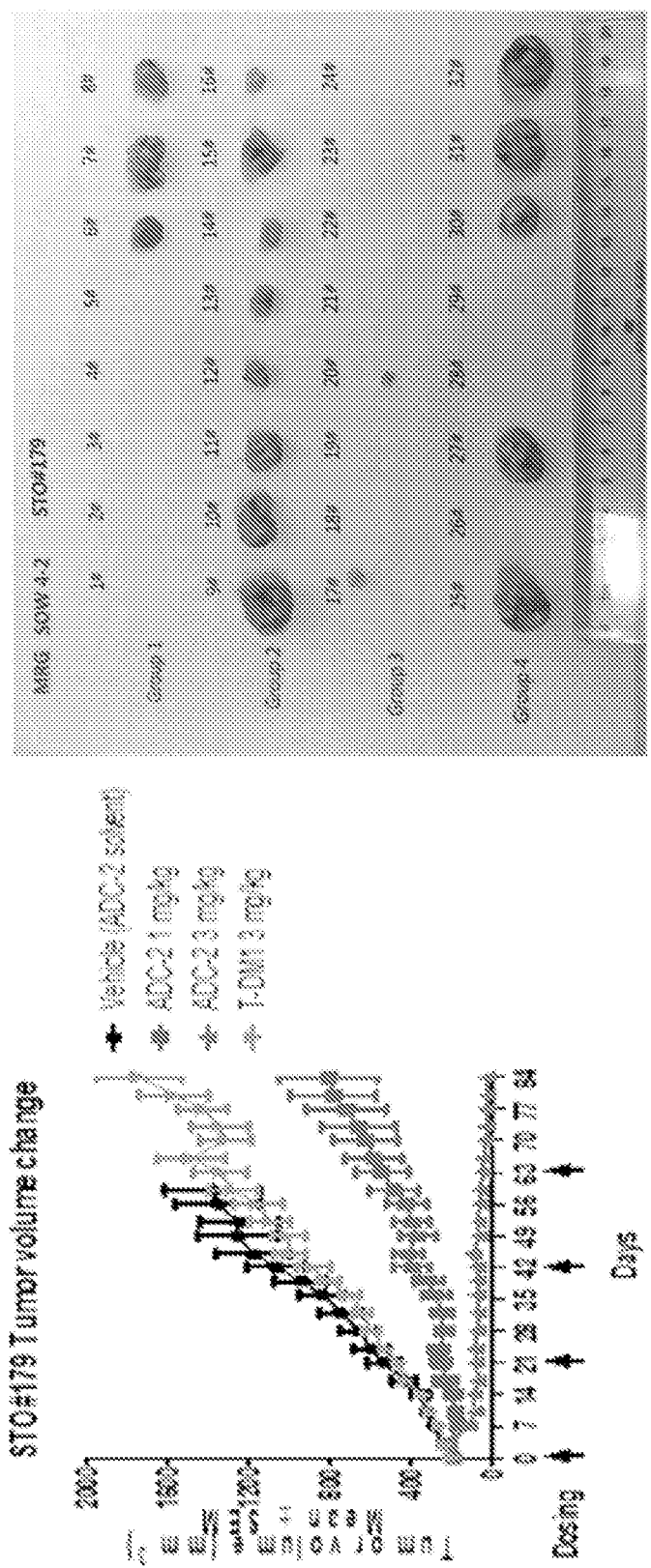

FIG. 13 shows the effect of MRG002 (ADC-2) and T-DM1 on the tumor volume of gastric cancer PDX model STO#179 (left) and the photo of tumors at the end of the study (right). Group 1 is vehicle (ADC-2 solvent), Group 2 is ADC-2 at a dose of 1 mg/kg, Group 3 is ADC-2 at a dose of 3 mg/kg, and Group 4 is T-DM1 at a dose of 3 mg/kg. Five tumor-bearing mice in the ADC-2 vehicle group had been euthanized before Day 84 for compliance with the animal welfare requirements (No. 1, 2, 3, 4 and 5 mice had tumor volume >2000 mm$^3$), therefore no picture of these tumors was taken.

Figure 14:
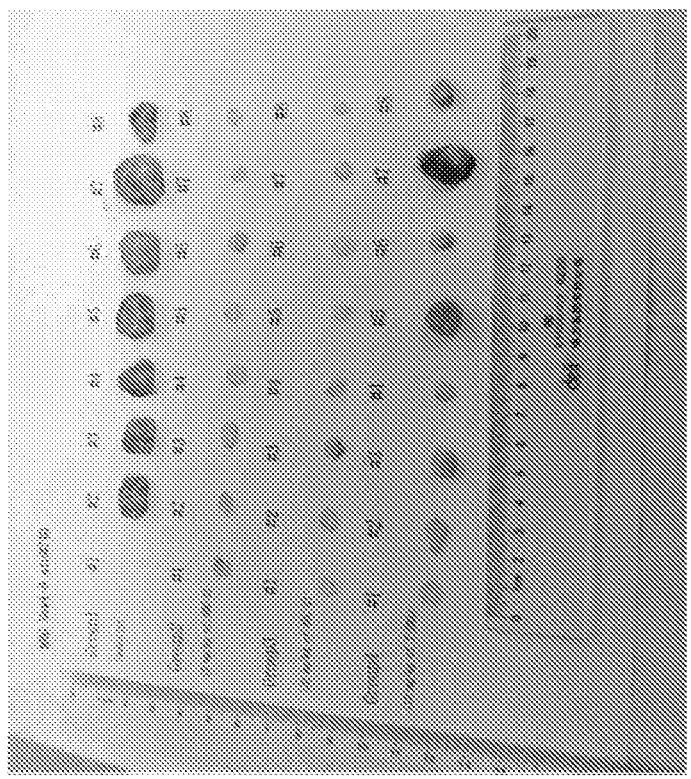
Figure 14:
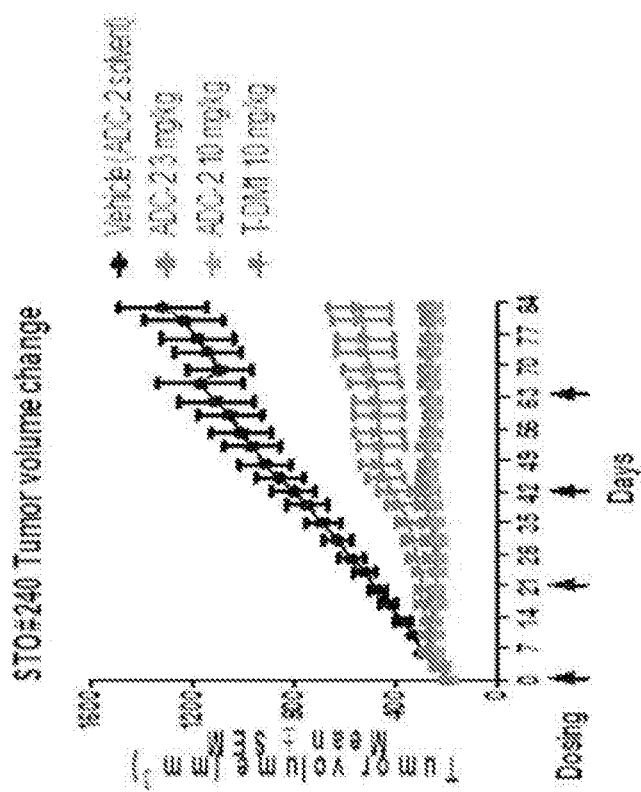

FIG. 14 shows the effect of MRG002 (ADC-2) and T-DM1 on the tumor volume of gastric cancer PDX model STO#240 (left) and the photo of tumors at the end of the study (right). Group 1 is vehicle (ADC-2 solvent), Group 2 is ADC-2 at a dose of 3 mg/kg, Group 3 is ADC-2 at a dose of 10 mg/kg, and Group 4 is T-DM1 at a dose of 10 mg/kg. No. 1 tumor-bearing mouse in the ADC-2 vehicle group had been euthanized before Day 84 for compliance with the animal welfare requirements (tumor volume >2000 mm$^3$), therefore no picture of its tumor was taken.

Figure 15:
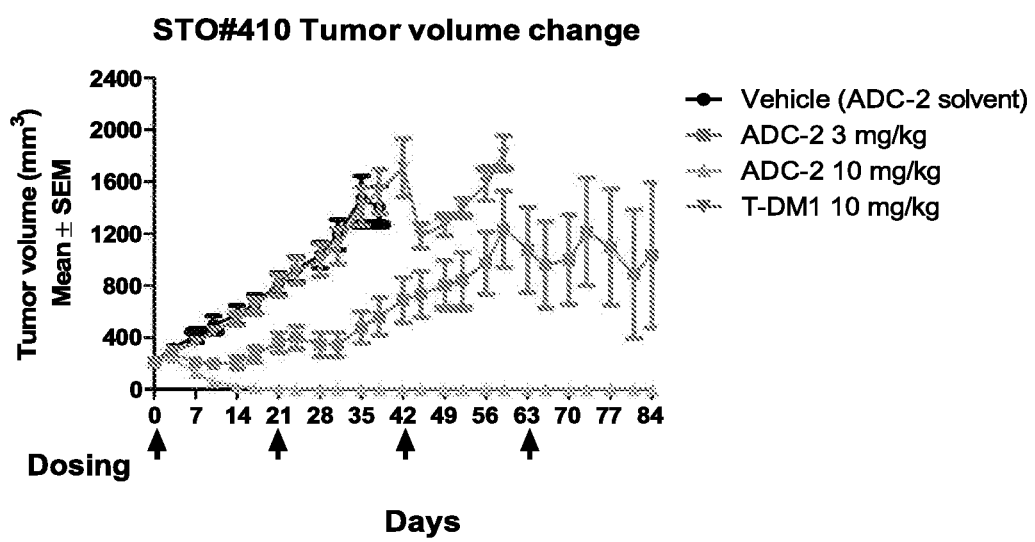

FIG. 15 shows the effect of MRG002 (ADC-2) and T-DM1 on the tumor volume of gastric cancer PDX model STO#410. All of the tumor-bearing mice in the vehicle (ADC-2 solvent) group were euthanized before Day 84 for compliance with the animal welfare requirements (tumor volume exceeded 2000 mm$^3$).

DETAILED DESCRIPTION

This document provides methods and materials useful for treating cancer. In some cases, ADCs provided herein can include an antibody targeting a tumor-associated antigen (e.g., a HER2 polypeptide) and an anti-cancer drug that can be administered to a mammal (e.g., a human) having a cancer expressing the antigen (e.g., a HER2-expressing cancer). For example, ADCs can include an anti-HER2 antibody (e.g., MAB802) and at least one (e.g., 2, 3, 4, 5, or more) molecule of one or more anti-cancer drugs (e.g., an auristatin derivative such as MMAE). In some cases, ADCs provided herein can be administered to a mammal (e.g., a human) having a cancer expressing the antigen (e.g., a HER2-expressing cancer) to treat the mammal. For example, one or more ADCs containing an anti-HER2 antibody and an anti-cancer drug can be administered to a mammal having a HER2-expressing cancer to reduce the severity of the cancer, to reduce a symptom of the cancer, and/or to reduce the number of cancer cells present within the mammal.

Antibody-Drug Conjugates

This document provides ADCs containing an anti-HER2 antibody (e.g., MAB802) and at least one (e.g., 2, 3, 4, 5, or more) molecule of one or more anti-cancer drugs (e.g., an auristatin derivative such as MMAE). Without being bound by theory, it is believed that ADCs described herein (e.g., MRG002) bind to HER2 receptors on tumor cell surface, are internalized via receptor-mediated endocytosis, release MMAE inside the lysosome, and cause suppression of tumor cell growth and/or cell death.

Antibodies

ADCs described herein (e.g., ADCs containing an anti-HER2 antibody and one or more anti-cancer drugs) can include any appropriate anti-HER2 antibody. As used herein, an "antibody" can be a complete antibody or an antigen-binding (Fab) fragment (e.g., a naturally occurring Fab or a synthetic Fab (e.g., a fusion protein such as a single-chain variable fragment (scFv)). For example, an anti-HER2 antibody can include any complete antibody or antibody fragment having binding affinity for a HER2 polypeptide. An anti-HER2 antibody can be any appropriate class and subclass (e.g., IgG such as IgG1, IgG2, IgG3, and IgG4; IgA such as IgA1 and IgA2; IgD; IgE; and IgM). In some cases, an anti-HER2 antibody can be an IgG (e.g., an IgG1) antibody. An anti-HER2 antibody can be a recombinant antibody. An anti-HER2 antibody can be a chimeric antibody (e.g., a humanized antibody). In some cases, an anti-HER2 antibody can be a humanized antibody. An anti-HER2 antibody can be a monoclonal antibody or a polyclonal antibody. In some cases, an antibody can be monoclonal antibody. An anti-HER2 antibody can be a monospecific antibody or a bispecific antibody. For example, in cases where an anti-HER2 antibody is a bispecific antibody, the bispecific anti-HER2 antibody can have binding affinity for a HER2 polypeptide and binding affinity for a second antigen. An anti-HER2 antibody can have binding affinity for a phosphorylated HER2 polypeptide or can have binding affinity for a non-phosphorylated HER2 polypeptide.

An anti-HER2 antibody can include any appropriate sequence. In some cases, an anti-HER2 antibody light chain can include the complementarity-determining regions (CDRs) set forth below:

(SEQ ID NO: 1)
ASQDVNTAVA;

(SEQ ID NO: 2)
SASFLYS;
and (SEQ ID NO: 3)
QQHYTTPPT.

For example, an anti-HER2 antibody light chain including CDRs set forth in SEQ ID NO:1, SEQ ID NO:2, and SEQ ID NO:3 can include an amino acid sequence set forth in SEQ ID NO:4.

SEQ ID NO: 4:
DIQMTQSPSSLSASVGDRVTITCRASQDVNTAVAWYQQK

PGKAPKLLIYSASFLYSGVPSRFSGSRSGTDFTLTISSL

QPEDFATYYCQQHYTTPPTFGQGTKVEIKRTVAAPSVFI

FPPSDEQLKSGTASVVCLLNNFYPREAKVQWKVDNALQS

GNSQESVTEQDSKDSTYSLSSTLTLSKADYEKHKVYACE

VTHQGLSSPVTKSFNRGEC

In some cases, an anti-HER2 antibody light chain can have an amino acid sequence that is at least 75 percent (e.g., at least 78%, at least 79%, at least 80%, at least 81%, at least 82%, at least 83%, at least 84%, at least 85%, at least 90%, at least 95%, at least 99%, or 100%) identical to the sequence set forth in SEQ ID NO:4. For example, an anti-HER2 antibody can have an amino acid sequence that is at least 75% identical to SEQ ID NO:4 and includes the CDRs set forth in SEQ ID NO:1, SEQ ID NO:2, and SEQ ID NO:3.

In some cases, an anti-HER2 antibody heavy chain can include the CDRs set forth below:

(SEQ ID NO: 5)
GFNIKDTYIH;

(SEQ ID NO: 6)
IYPTNGYTRYADSVK;
and (SEQ ID NO: 7)
WGGDGFYAMDY.

For example, an anti-HER2 antibody heavy chain including CDRs set forth in SEQ ID NO: 5, SEQ ID NO:6, and SEQ ID NO:7 can include an amino acid sequence set forth in SEQ ID NO:8, SEQ ID NO:9, or SEQ ID NO:10.

SEQ ID NO: 8
EVQLVESGGGLVQPGGSLRLSCAASGFNIKDTYIHWVRQAP

GKGLEWVARIYPTNGYTRYADSVKGRFTISADTSKNTAYLQ

MNSLRAEDTAVYYCSRWGGDGFYAMDYWGQGTLVTVSSASS

TKGPSVFPLAPSSKSTSGGTAALGCLVKDYFPEPVTVSWNS

GALTSGVHTFPAVLQSSGLYSLSSVVTVPSSSLGTQTYICN

VNHKPSNTKVDKKVEP

SEQ ID NO: 9
EVQLVESGGGLVQPGGSLRLSCAASGFNIKDTYIHWVRQAP

GKGLEWVARIYPTNGYTRYADSVKGRFTISADTSKNTAYLQ

MNSLRAEDTAVYYCSRWGGDGFYAMDYWGQGTLVTVSSAST

KGPSVFPLAPSSKSTSGGTAALGCLVKDYFPEPVTVSWNSG

ALTSGVHTFPAVLQSSGLYSLSSVVTVPSSSLGTQTYICNV

NHKPSNTKVDKKVEPKSCDKTHTCPPCPAPELLGGPSVFLF

PPKPKDTLMISRTPEVTCVVVDVSHEDPEVKFNWYVDGVEV

HNAKTKPREEQYNSTYRVVSVLTVLHQDWLNGKEYKCKVSN

KALPAPIEKTISKAKGQPREPQVYTLPPSREEMTKNQVSLT

CLVKGFYPSDIAVEWESNGQPENNYKTTPPVLDSDGSFFLY

SKLTVDKSRWQQGNVFSCSVMHEALHNHYTQKSLSLSPGK

SEQ ID NO: 10
EVQLVESGGGLVQPGGSLRLSCAASGFNIKDTYIHWVRQAP

GKGLEWVARIYPTNGYTRYADSVKGRFTISADTSKNTAYLQ

MNSLRAEDTAVYYCSRWGGDGFYAMDYWGQGTLVTVSSAST

KGPSVFPLAPSSKSTSGGTAALGCLVKDYFPEPVTVSWNSG

ALTSGVHTFPAVLQSSGLYSLSSVVTVPSSSLGTQTYICNV

NHKPSNTKVDKKVEPPKSCDKTHTCPPCPAPELLGGPSVFL

FPPKPKDTLMISRTPEVTCVVVDVSHEDPEVKFNWYVDGVE

VHNAKTKPREEQYNSTYRVVSVLTVLHQDWLNGKEYKCKVS

NKALPAPIEKTISKAKGQPREPQVYTLPPSRDELTKNQVSL

TCLVKGFYPSDIAVEWESNGQPENNYKTTPPVLDSDGSFFL

YSKLTVDKSRWQQGNVESCSVMHEALHNHYTQKSLSLSPGK

In some cases, an anti-HER2 antibody heavy chain can have an amino acid sequence that is at least 75 percent (e.g., at least 78%, at least 79%, at least 80%, at least 81%, at least 82%, at least 83%, at least 84%, at least 85%, at least 90%, at least 95%, at least 99%, or 100%) identical to the sequence set forth in any one of SEQ ID NO: 8 to SEQ ID NO:10. For example, an anti-HER2 antibody can have an amino acid sequence that is at least 75% identical to SEQ ID NO:9 and includes the CDRs set forth in SEQ ID NO:5, SEQ ID NO:6, and SEQ ID NO:7. For example, an anti-HER2 antibody can have an amino acid sequence that is at least 75% identical to SEQ ID NO:9, includes the CDRs set forth in SEQ ID NO:5, SEQ ID NO:6, and SEQ ID NO:7, and has an EEM sequence at residues 359-361.

Examples of anti-HER2 antibodies that can be used in an ADC described herein include, without limitation, MAB802, trastuzumab, pertuzumab, and hertuzumab. For example, an ADC described herein can include a MAB802 antibody.

This document also provides nucleic acids encoding anti-HER2 antibodies described herein as well as constructs (e.g., expression constructs) for expressing nucleic acids encoding anti-HER2 antibodies described herein.

In some cases, an anti-HER2 antibody can have an increased level of fucosylation and/or a decreased level of afucosylation (e.g., relative to other anti-HER2 antibodies, such as anti-HER2 antibodies used in current FDA-approved HER2-targeted therapies (e.g., trastuzumab)).

As used herein, the percent fucosylation refers to the molar percentage of glycans attached to the antibody that contain fucose (i.e., the percentage ratio of the molar amount of the fucosylated glycans to the total molar amount of both fucosylated and non-fucosylated glycans).

As used herein, the percent afucosylation refers to the molar percentage of glycans attached to the antibody that do not contain fucose (i.e., the percentage ratio of the molar amount of the non-fucosylated glycans to the total molar amount of both fucosylated and non-fucosylated glycans).

Figures 2A, 2B:
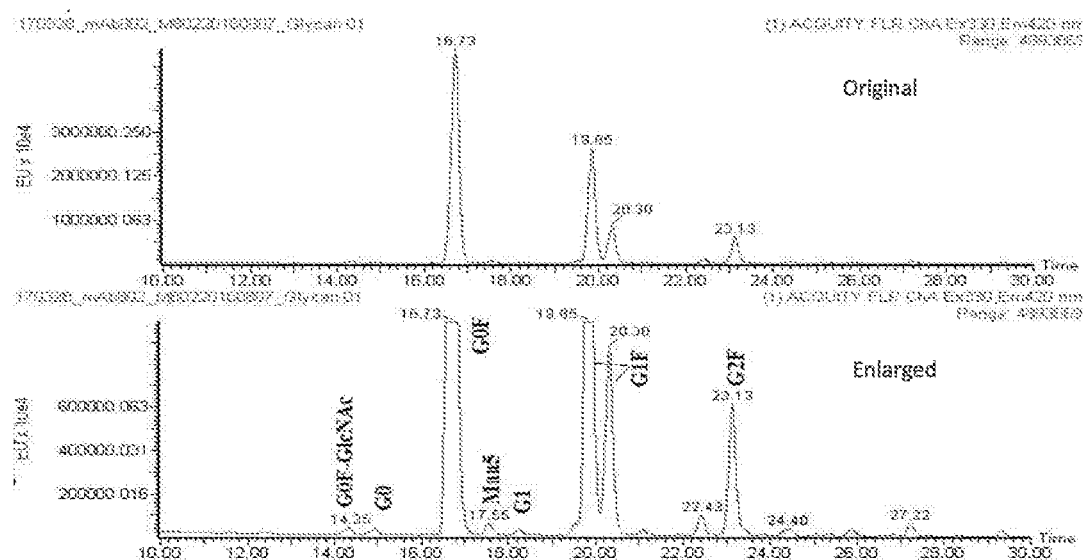
FIG. 2A contains a schematic of glycan types. Among these glycans, those with red triangles (standing for fucose) are fucosylated, while others are not.
FIG. 2B contains a fluorescence chromatogram showing the glycan fractions present on MAB802.

Examples of glycan types can be as shown in FIG. 2A. For example, with reference to FIG. 2A, the percent fucosylation can be determined as a ratio of the total amount of fucorylated glycans (G0F-GlcNAc. G0F, G1F and G2F) divided by the total amount of all the glycans (G0F-GlcNAc. G0, G0F, Man5, G1, G1F and G2F). Similarly, the percent afucosylation can be determined as the ratio of the total amount of the non-fucosylated glycans (G0, Man5 and G1) to divided by the total amount of all the glycans (G0F-GlcNAc. G0, G0F, Man5, G1, G1F and G2F).

In some cases, an anti-HER2 antibody can have an increased level of fucosylation and/or a decreased level of afucosylation in the Fc region of the antibody. Any appropriate method can be used to determine the amount of fucosylation on an antibody. For example, a glycosylation analysis (e.g., an N-glycan analysis) can be performed using HPLC (see, e.g., the Examples) or as described elsewhere (see, e.g., EUROPEAN PHARMACOPOEIA 8.0; 2.2.59. Glycan analysis of glycoproteins).

In some cases, an anti-HER2 antibody can have greater than about 86% fucosylation (e.g., greater than about 87%, greater than about 88%, greater than about 89%, greater than about 90%, greater than about 91%, greater than about 92%, greater than about 93%, greater than about 94%, greater than about 95%, greater than about 95%, greater than about 96%, greater than about 98%, greater than about 99%, or about 100% fucosylation).

In some cases, an anti-HER2 antibody can have from about 86% to about 100% fucosylation (e.g., from about 86% to about 99%, from about 86% to about 98%, from about 86% to about 97%, from about 86% to about 95%, from about 86% to about 92%, from about 86% to about 90%, from about 86% to about 88%, from about 87% to about 100%, from about 88% to about 100%, from about 89% to about 100%, from about 90% to about 100%, from about 93% to about 100%, from about 95% to about 100%, from about 97% to about 100%, from about 88% to about 97%, from about 90% to about 95%, from about 87% to about 92%, or from about 92% to about 98%, or from about 92% to about 99% fucosylation). For example, an anti-HER2 antibody can have about 97.77% or about 98% afucosylation.

In some cases, an anti-HER2 antibody can have less than about 14% afucosylation (e.g., less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, or less than about 0.5% afucosylation). In some cases, an anti-HER2 antibody can have from about 0% to about 14% afucosylation (e.g., from about 0% to about 12%, from about 0% to about 10%, from about 0% to about 9%, from about 0% to about 8%, from about 0% to about 7%, from about 0% to about 6%, from about 0% to about 5%, from about 0% to about 4%, from about 0% to about 3%, from about 0% to about 2%, from about 0% to about 1%, from about 1% to about 14%, from about 3% to about 14%, from about 5% to about 14%, from about 7% to about 14%, from about 10% to about 14%, from about 12% to about 14%, from about 1% to about 10%, from about 2% to about 7%, from about 3% to about 6%, from about 0.5% to about 5%, from about 1% to about 5%, from about 1.5% to about 4%, or from about 2% to about 3% afucosylation). For example, an anti-HER2 antibody can have about 2.23% afucosylation.

In some cases, an anti-HER2 antibody can be modified to have an increased level of fucosylation and/or to have a decreased level of afucosylation. Any appropriate method can be used to alter (e.g., increase or decrease) the fucosylation level of an anti-HER2 antibody. For example, the level of fucosylation on an anti-HER2 antibody can be altered, for example, by modifying culture medium osmolality. For example, the level of fucosylation on an anti-HER2 antibody can be increased using, for example, a fucosyltransferase. For example, the level of fucosylation on an anti-HER2 antibody can be decreased using, for example, a fucosyltransferase inhibitor. In some cases, an anti-HER2 antibody can be modified to have an increased level of fucosylation and/or to have a decreased level of afucosylation as described elsewhere (see, e.g., Konno et al., 2012 *Cytotechnology*, 64:249-265; and Yamane-Ohnuki et al., 2009 *mAbs*, 1:3).

An anti-HER2 antibody can have decreased antibody-dependent cellular cytotoxicity (ADCC) activity (e.g., relative to other anti-HER2 antibodies, such as anti-HER2 antibodies used in current FDA-approved HER2-targeted therapies (e.g., trastuzumab)). For example, an anti-HER2 antibody can have ADCC activity leading to decreased cell lysis. In some cases, an anti-HER2 antibody can have ADCC activity leading to less than about 30% cell lysis (e.g., less than about 30%, less than about 29%, less than about 29%, less than about 28%, less than about 27%, less than about 26%, less than about 25%, less than about 24%, less than about 23%, less than about 22%, less than about 21%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, or less than about 5%). In some cases, an anti-HER2 antibody can have ADCC activity leading to from about 0% to about 30% cell lysis (e.g., from about 0% to about 28%, from about 0% to about 25%, from about 0% to about 22%, from about 0% to about 20%, from about 0% to about 17%, from about 0% to about 15%, from about 0% to about 13%, from about 0% to about 10%, from about 0% to about 5%, from about 2% to about 30%, from about 5% to about 30%, from about 10% to about 30%, from about 12% to about 30%, from about 15% to about 30%, from about 18% to about 30%, from about 20% to about 30%, from about 22% to about 30%, from about 25% to about 30%, from about 3% to about 25%, from about 5% to about 22%, from about 8% to about 20%, from about 10% to about 18%, or from about 13% to about 16% cell lysis). For example, an anti-HER2 antibody can have ADCC activity leading to from about 13.9% to about 15.7% cell lysis. For example, an anti-HER2 antibody can have ADCC activity leading to about 14.8% cell lysis.

An anti-HER2 antibody can have decreased CD16 binding affinity (e.g., relative to other anti-HER2 antibodies, such as anti-HER2 antibodies used in current FDA-approved HER2-targeted therapies (e.g., trastuzumab)). The CD16 can be a human CD16. The CD16 can be a CD16a or a CD16b form of CD16. For example, the CD16 can be a CD16a. In some cases, the CD16 can have a valine residue at position 176 (e.g., a 176Val CD16). In some cases, the CD16 can have a phenylalanine residue at position 176 (e.g., a 176Phe CD16). In some cases, an anti-HER2 antibody can have a CD16 binding affinity having an equilibrium dissociation constant (KD) value of greater than about $2.5 \times 10^{-08}$ M (e.g., greater than about $2.7 \times 10^{-08}$ M, greater than about $3.0 \times 10^{-08}$ M, greater than about $3.2 \times 10^{-08}$ M, greater than about $3.5 \times 10^{-08}$ M, greater than about $4.0 \times 10^{-08}$ M, greater than about $4.3 \times 10^{-08}$ M, greater than about $4.5 \times 10^{-08}$ M, greater than about $4.8 \times 10^{-08}$ M, greater than about $5.0 \times 10^{-08}$ M, greater than about $5.3 \times 10^{-08}$ M, greater than about $5.5 \times 10^{-08}$ M, greater than about $5.7 \times 10^{-08}$ M, greater than about $6.0 \times 10^{-08}$ M, greater than about $6.2 \times 10^{-08}$ M, greater than about $6.5 \times 10^{-08}$ M, greater than about $6.8 \times 10^{-08}$ M, greater than about $2.5 \times 10^{-08}$ M, greater than about $7.0 \times 10^{-08}$ M, greater than about $7.3 \times 10^{-08}$ M, greater than about $7.5 \times 10^{-08}$ M, greater than about $7.8 \times 10^{-08}$ M, greater than about $8.0 \times 10^{-08}$ M, greater than about $8.2 \times 10^{-08}$ M, greater than about $8.5 \times 10^{-08}$ M, greater than about $8.7 \times 10^{-08}$ M, greater than about $9.0 \times 10^{-08}$ M, or greater than about $9.5 \times 10^{-08}$ M). In some cases, an anti-HER2 antibody can have a CD16 binding affinity having a KD value of from about $2.5 \times 10^{-08}$ M to about $10.0 \times 10^{-08}$ M (e.g., from about $3.0 \times 10^{-08}$ M to about $10.0 \times 10^{-08}$ M, from about $3.5 \times 10^{-08}$ M to about $10.0 \times 10^{-08}$ M, from about $4.0 \times 10^{-08}$ M to about $10.0 \times 10^{-08}$ M, from about $4.5 \times 10^{-08}$ M to about $10.0 \times 10^{-08}$ M, from about $5.0 \times 10^{-08}$ M to about $10.0 \times 10^{-08}$ M, from about $5.5 \times 10^{-08}$ M to about $10.0 \times 10^{-08}$ M, from about $6.0 \times 10^{-08}$ M to about $10.0 \times 10^{-08}$ M, from about $6.5 \times 10^{-08}$ M to about $10.0 \times 10^{-08}$ M, from about $6.8 \times 10^{-08}$ M to about $10.0 \times 10^{-08}$ M, from about $7.0 \times 10^{-08}$ M to about $10.0 \times 10^{-08}$ M, from about $7.2 \times 10^{-08}$ M to about $10.0 \times 10^{-08}$ M, from about $7.5 \times 10^{-08}$ M to about $10.0 \times 10^{-08}$ M, from about $7.8 \times 10^{-08}$ M to about $10.0 \times 10^{-08}$ M, from about $8.0 \times 10^{-08}$ M to about $10.0 \times 10^{-08}$ M, from about $8.2 \times 10^{-08}$ M to about $10.0 \times 10^{-08}$ M, from about $8.5 \times 10^{-08}$ M to about $10.0 \times 10^{-08}$ M, from about $2.5 \times 10^{-08}$ M to about $9.5 \times 10^{-08}$ M, from about $2.5 \times 10^{-08}$ M to about $9.0 \times 10^{-08}$ M, from about $2.5 \times 10^{-08}$ M to about $8.8 \times 10^{-08}$ M, from about $2.5 \times 10^{-08}$ M to about $8.5 \times 10^{-08}$ M, from about $2.5 \times 10^{-08}$ M to about $8.2 \times 10^{-08}$ M, from about $2.5 \times 10^{-08}$ M to about $8.0 \times 10^{-08}$ M, from about $2.5 \times 10^{-08}$ M to about $7.7 \times 10^{-08}$ M, from about $2.5 \times 10^{-08}$ M to about $7.5 \times 10^{-08}$ M, from about $2.5 \times 10^{-08}$ M to about $7.3 \times 10^{-08}$ M, from about $2.5 \times 10^{-08}$ M to about $7.0 \times 10^{-08}$ M, from about $2.5 \times 10^{-08}$ M to about $6.8 \times 10^{-08}$ M, from about $2.5 \times 10^{-08}$ M to about $6.5 \times 10^{-08}$ M, from about $3.0 \times 10^{-08}$ M to about $9.5 \times 10^{-08}$ M, from about $3.5 \times 10^{-08}$ M to about $9.0 \times 10^{-08}$ M, from about $4.0 \times 10^{-08}$ M to about $8.8 \times 10^{-08}$ M, from about $4.5 \times 10^{-08}$ M to about $8.5 \times 10^{-08}$ M, from about $5.0 \times 10^{-08}$ M to about $8.2 \times 10^{-08}$ M, from about $5.5 \times 10^{-08}$ M to about $8.0 \times 10^{-08}$ M, from about $6.0 \times 10^{-08}$ M to about $7.8 \times 10^{-08}$ M, or from about $6.5 \times 10^{-08}$ M to about $7.5 \times 10^{-08}$ M). For example, an anti-HER2 antibody can have a CD16 binding affinity (e.g., a binding affinity for a human 176Val CD16a) having a KD value of from about $6.9 \times 10^{-08}$ M (e.g., about $6.988 \times 10^{-08}$ M) to about $7.1 \times 10^{-08}$ M (e.g., about $7.089 \times 10^{-08}$ M). For example, an anti-HER2 antibody can have a CD16 binding affinity (e.g., a binding affinity for a human 176Phe CD16a) having a KD value of from about $6.6 \times 10^{-07}$M (e.g., about $6.620 \times 10^{-07}$M) to about $6.9 \times 10^{-07}$ M (e.g., about $6.894 \times 10^{-07}$M).

Anti-Cancer Drugs

ADCs described herein (e.g., ADCs containing an anti-HER2 antibody and one or more anti-cancer drugs) can include any appropriate anti-cancer drugs. In some cases, the one or more anti-cancer drugs can include one or more molecules of a single anti-cancer drug (e.g., per anti-HER2 antibody). In some cases, the one or more anti-cancer drugs can include one or more molecules of two or more different anti-cancer drugs (e.g., per anti-HER2 antibody). An anti-cancer drug can be a cytotoxic agent. An anti-cancer drug can be an antimicrotubule agent. An anti-cancer drug can be a microtubule-formation inhibitor. An anti-cancer drug can be an antineoplastic agent. An anti-cancer drug can be naturally occurring compound or a synthetic drug. Examples of anti-cancer drugs that can be used in ADCs described herein include, without limitation, auristatins (e.g., monomethyl auristatin E (MMAE) and monomethyl auristatin F (MMAF)), maytansines (e.g., mertansine (DM1), maitansine (INN), and maytansine (USAN)), pyrrolobenzodiazepines (PBDs), duocarmycins, calicheamicins, SN-38, amanitin, and eribulin, or derivatives thereof.

For example, ADCs containing an anti-HER2 antibody and one or more anti-cancer drugs can include one or more molecules of MMAE per molecule of the antibody.

Linkers

ADCs described herein (e.g., ADCs containing an anti-HER2 antibody and one or more anti-cancer drugs) can include one or more linkers connecting the anti-HER2 antibody and the one or more anti-cancer drugs. A linker can be any appropriate linker.

Since a function of the linker is to provide a physical connection between the antibody and drug, a wide variety of chemical groups can, in principle, serve as a linker. The linker typically a divalent organic linking group where one valency represents the point of attachment to the antibody and one valency represents the attachment to the drug.

A linker can be a cleavable linker or a non-cleavable linker. In some cases, a linker can be a cleavable linker. For example, a cleavable linker can be cleaved by an enzyme such as cathepsin B. A linker can be a peptide linker that includes one or more (e.g., 1, 2, 3, 4, or more) amino acids (e.g., natural amino acids or non-natural amino acids). For example, a peptide linker can include one or more of valine and/or citruline.

A linker can also be a biodegradable linker. Examples of linkers that can be used in ADCs described herein include, without limitation, valine citruline dipeptide linkers (vcLinkers), disulfide linkers, thioether linkers, SPP, SMCC, SPDB, MC, acetyl butyrate, and CL2A, and/or hadrazone, PEG4-Mal,b-glucuronide. In some cases, a linker can be as described elsewhere (see, e.g., Donaghy, 2016 *mAbs*, 8:659-71).

For example, ADCs containing an anti-HER2 antibody and one or more anti-cancer drugs can include a vcLinker connecting the anti-HER2 antibody and the one or more anti-cancer drugs.

In some embodiments, the linker is of the formula:

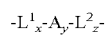

wherein:

$L^1$ is a first divalent chemical group;

x is 0 or 1;

Ay is a an amino acid or peptide group, wherein:

each A is an independently selected amino acid group;

y is 0, 1, 2, 3, 4, 5, 6, 7, 8, 9, 10, 11, or 12;

$L^2$ is a second divalent chemical group; and z is 0 or 1.

$L^1$, when present, links the antibody to an amino acid or peptide moiety of formula $-A_y-$. The antibody is attached to $L^1$ via a functional group that can form a suitable covalent bond such as a mercapto (SH), amino, hydroxyl, carboxy, or carboxyl. The functional group can be present on the antibody as originally obtained or introduced by chemical manipulation. For example, mercapto groups can be generated by reduction of an intramolecular disulfide bond. Suitable amino groups can include an amino group group of a lysine moiety of the antibody.

Examples of suitable $L^1$ groups include, e.g.: —O—, —S—, —S(O)—, —S(O)$_2$—, —C(O)—, —NH—, —N(C$_1$-C$_6$)alkyl, —NHC(O)—, —C(O)NH—, —O(CO)—, —C(O) O—, —O(CO)NH—, —NHC(O)O—, —O(CO)O—, —NHC(O)NH—, —O(C$_1$-C$_6$)alkylene-, —S(C$_1$-C$_6$)alkylene-, —S(O)(C$_1$-C$_6$)alkylene-, —S(O)$_2$(C$_1$-C$_6$)alkylene-, —C(O)(C$_1$-C$_6$)alkylene-, —NH((C$_1$-C$_6$)alkylene)C(O)—, —C(O)((C$_1$-C$_6$)alkylene)C(O)—, —C(O)((C$_1$-C$_6$)alkylene)NH—, —O(CO)—, —C(O)O—, —O(CO)NH—, —NHC(O)O—, —O(CO)O—, —NHC(O)NH—, unsubstituted-(C$_1$-C$_{10}$)alkylene-, unsubstituted-(C$_1$-C$_{10}$)heteroalkylene, or —(C$_1$-C$_{10}$)alkylene or —(C$_1$-C$_{10}$)heteroalkylene substituted with one or more (e.g., 1, 2, 3, 4 or 5 substituents) independently selected from the group consisting of (C$_1$-C$_6$)alkyl, (C$_2$-C$_6$)alkenyl, (C$_2$-C$_6$)alkynyl, halogen, (C$_1$-C$_6$)haloalkyl, —CN, —NO$_2$, —C(=O)R, —OC(=O)Ar, —C(=O)OR, —C(=O)NR$_2$, —C(=NR)NR$_2$, —OR, —Ar, —OAr, —((C$_1$-C$_6$)alkylene)Ar, —O((C$_1$-C$_6$)alkylene)Ar, —OC(=O)(C$_1$-C$_6$)alkyl, —OC(=O)O(C$_1$-C$_6$)alkyl, —OC(=O)NR$_2$, —NR$_2$, —NRAr, —NR((C$_1$-C$_6$)alkylene)Ar, —NRC(=O)R, —NRC(=O)Ar, —NRC(=O)O(C$_1$-C$_6$)alkyl, —NRC(=O)NR$_2$, —NRSO$_2$R, —SR, —S(O)R, —SO$_2$R, —OSO$_2$(C$_1$-C$_6$)alkyl, —SO$_2$NR$_2$, (C$_1$-C$_8$)perfluoroalkyl, —(C$_2$-C$_6$)alkylene-OR, —O(C$_2$-C$_6$)alkylene-N((C$_1$-C$_6$)alkyl)$_2$, —P(=O)(OR)$_2$, —OP(=O)(OR)$_2$, oxo and sulfido, wherein each R group is hydrogen or (C$_1$-C$_6$ alkyl), e.g., methyl and wherein each Ar is independently unsubstituted aryl or heteroaryl or aryl or heteroaryl substituted with one or more of (C$_1$-C$_6$)alkyl, (C$_2$-C$_6$)alkenyl, (C$_2$-C$_6$)alkynyl, halogen, (C$_1$-C$_6$)haloalkyl, —CN, —NO$_2$, —C(=O)R, —C(=O)OR, —C(=O)NR$_2$, —C(=NR)NR$_2$, —OR, —OC(=O)(C$_1$-C$_6$)alkyl, —OC(=O)O(C$_1$-C$_6$)alkyl, —OC(=O)NR$_2$, —NR$_2$, —NRC(=O)R, —NRC(=O)O(C$_1$-C$_6$)alkyl, —NRC(=O)NR$_2$, —NRS$_2$R, —SR, —S(O)R, —SO$_2$R, —OSO$_2$(C$_1$-C$_6$)alkyl, —SO$_2$NR$_2$, (C$_1$-C$_6$)perfluoroalkyl, —(C$_2$-C$_6$)alkylene-OR, —O(C$_2$-C$_6$)alkylene-N((C$_1$-C$_6$)alkyl)$_2$, —P(=O)(OR)$_2$, —OP(=O)(OR)$_2$ wherein each R group is hydrogen or (C$_1$-C$_6$ alkyl). In addition, —(C$_1$-C$_{10}$)alkylene- and —(C$_1$-C$_{10}$)heteroalkylene can be substituted by one or more oxo groups (C=O) and the nitrogen and sulfur atoms of a heteroalkylene group can optionally be oxidized (e.g., to form S(O), —S(O)$_2$—, or N-oxide). Suitable heteroalkylene groups can include one or more 1,2-dioxyethylene units —(O—CH$_2$CH$_2$)$_n$—, where n is an integer, e.g., 1, 2, 3, 4 or 5). The —(C$_1$-C$_{10}$)alkylene- and —(C$_1$-C$_{10}$)heteroalkylene also include —(C$_1$-C$_6$)alkylene- and —(C$_1$-C$_6$)heteroalkylene and —(C$_1$-C$_3$)alkylene- and —(C$_1$-C$_3$)heteroalkylene $L_1$ may be a group of the formula:

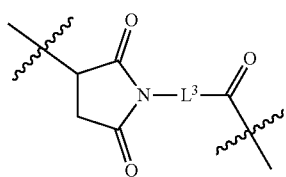

which may be attached to the antibody, e.g., via S or NH, so that the linking moiety (including the functional group attaching L to the antibody) is of the formula:

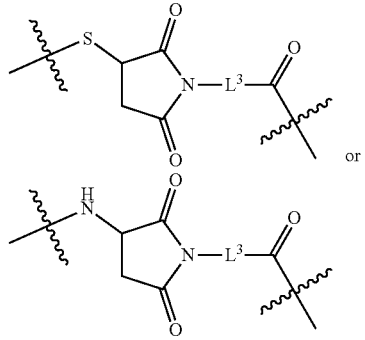

Suitable $L^3$ groups include groups of formula —(C$_1$-C$_{10}$) alkylene- or —(C$_1$-C$_{10}$)heteroalkylene, such as —CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —CH$_2$CH$_2$OCH$_2$—, and —CH$_2$CH$_2$OCH$_2$CH$_2$OCH$_2$—. In some embodiments, $L^3$ is of the formula —(CH$_2$)$_5$—.

The amino acid or peptide group, when present, is an amino acid, or a dipeptide, tripeptide, tetrapeptide, pentapeptide, hexapeptide, heptapeptide, octapeptide, nonapeptide, decapeptide, undecapeptide or dodecapeptide unit.

In some embodiments, each A is a group of the formula:

—NH—CH(A$^1$)-C(O)—

In some embodiments, each A1 is independently selected from hydrogen, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH(OH)CH$_2$NH$_2$, 2-pyridylmethyl, 3-pyridylmethyl, 4-pyridylmethyl-, phenyl, cyclohexyl, 2-(phenyl)ethyl, 2-(4-hydroxyphenyl)ethyl, (imidazol-4-yl)methyl, and indol-3-yl methyl.

In some embodiments, each A is an amino acid moiety selected from alanine, citrulline, cysteine, aspartic acid, glutamic acid, phenylalanine, glycine, histidine, isoleucine, lysine, leucine, methionine, asparagine, pyrrolysine, proline, glutamine, arginine, serine, threonine, selenocyseine, valine, tryptophan, and tyrosine.

The amino acid groups forming A can be of R or S (or D or L) configuration. In some embodiments, the amino acids can be of naturally occurring configuration (i.e., S or L; or R/L in the case of cysteine).

In some embodiments, A is a dipeptide of the following formula:

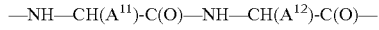
—NH—CH(A$^{11}$)-C(O)—NH—CH(A$^{12}$)-C(O)— wherein A$^{11}$ and A$^{12}$ are independently selected from groups of formula A1 as defined above. In some embodiments A$^{11}$ can be methyl and A$^{12}$ can be (CH$_2$)$_4$NH$_2$. In some embodiments A$^{11}$ can be isopropyl and A$^{12}$ can be $(CH_2)_4NH_2$. In some embodiments $A^{11}$ can be benzyl and $A^{12}$ can be $(CH_2)_4NH_2$. In some embodiments $A^{11}$ can be indol-3-ylmethyl and $A^{12}$ can be $(CH_2)_4NH_2$. In some embodiments $A^{11}$ can be methyl and $A^{12}$ can be $(CH_2)_3NHCONH_2$. In some embodiments $A^{11}$ can be isopropyl and $A^{12}$ can be $(CH_2)_3NHCONH_2$. In some embodiments $A^{11}$ can be benzyl and $A^{12}$ can be $(CH_2)_3NHCONH_2$. In some embodiments $A^{11}$ can be indol-3-ylmethyl and $A^{12}$ can be $(CH_2)_3NHCONH_2$.

$L^2$, when present, links the amino acid or peptide moiety of formula -$A_y$- to the drug molecule. Examples of suitable $L^2$ groups include,
e.g.: —O—, —S—, —S(O)—, —S(O)$_2$—, —C(O)—, —NH—, —N($C_1$-$C_6$)alkyl, —NHC(O)—, —C(O)NH—, —O(CO)—, —C(O) O—, —O(CO)NH—, —NHC(O)O—, —O(CO)O—, —NHC(O)NH—, —O($C_1$-$C_6$)alkylene-, —S($C_1$-$C_6$)alkylene-, —S(O)($C_1$-$C_6$)alkylene-, —S(O)$_2$($C_1$-$C_6$)alkylene-, —C(O)($C_1$-$C_6$)alkylene-, —NH(($C_1$-$C_6$)alkylene)C(O)—, —C(O)(($C_1$-$C_6$)alkylene)C(O)—, —C(O)(($C_1$-$C_6$)alkylene)NH—, —O(CO)—, —C(O)O—, —O(CO)NH—, —NHC(O)O—, —O(CO)O—, —NHC(O)NH—, unsubstituted-($C_1$-$C_{10}$)alkylene-, unsubstituted-($C_1$-$C_{10}$)heteroalkylene, or —($C_1$-$C_{10}$)alkylene or —($C_1$-$C_{10}$)heteroalkylene substituted with one or more (e.g., 1, 2, 3, 4 or 5 substituents) independently selected from the group consisting of ($C_1$-$C_6$)alkyl, ($C_2$-$C_6$)alkenyl, ($C_2$-$C_6$)alkynyl, halogen, ($C_1$-$C_6$)haloalkyl, —CN, —NO$_2$, —C(=O)R, —OC(=O)Ar, —C(=O)OR, —C(=O)NR$_2$, —C(=NR)NR$_2$, —OR, —Ar, —OAr, —(($C_1$-$C_6$)alkylene)Ar, —O(($C_1$-$C_6$)alkylene)Ar, —OC(=O)($C_1$-$C_6$)alkyl, —OC(=O)O($C_1$-$C_6$)alkyl, —OC(=O)NR$_2$, —NR$_2$, —NRAr, —NR(($C_1$-$C_6$)alkylene)Ar, —NRC(=O)R, —NRC(=O)Ar, —NRC(=O)O($C_1$-$C_6$)alkyl, —NRC(=O)NR$_2$, —NRSO$_2$R, —SR, —S(O)R, —SO$_2$R, —OSO$_2$($C_1$-$C_6$)alkyl, —SO$_2$NR$_2$, ($C_1$-$C_8$)perfluoroalkyl, —($C_2$-$C_6$)alkylene-OR, —O($C_2$-$C_6$)alkylene-N(($C_1$-$C_6$)alkyl)$_2$, —P(=O)(OR)$_2$, —OP(=O)(OR)$_2$, oxo and sulfido, wherein each R group is hydrogen or ($C_1$-$C_6$ alkyl), e.g., methyl and wherein each Ar is independently unsubstituted aryl or heteroaryl or aryl or heteroaryl substituted with one or more of ($C_1$-$C_6$) alkyl, ($C_2$-$C_6$)alkenyl, ($C_2$-$C_6$)alkynyl, halogen, ($C_1$-$C_6$)haloalkyl, —CN, —NO$_2$, —C(=O)R, —C(=O)OR, —C(=O)NR$_2$, —C(=NR)NR$_2$, —OR, —OC(=O)($C_1$-$C_6$) alkyl, —OC(=O)O($C_1$-$C_6$)alkyl, —OC(=O)NR$_2$, —NR$_2$, —NRC(=O)R, —NRC(=O)O($C_1$-$C_6$)alkyl, —NRC(=O) NR$_2$, —NRSO$_2$R, —SR, —S(O)R, —SO$_2$R, —OSO$_2$($C_1$-$C_6$)alkyl, —SO$_2$NR$_2$, ($C_1$-$C_8$)perfluoroalkyl, —($C_2$-$C_6$)alkylene-OR, —O($C_2$-$C_6$)alkylene-N(($C_1$-$C_6$)alkyl)$_2$, —P(=O)(OR)$_2$, —OP(=O)(OR)$_2$ wherein each R group is hydrogen or ($C_1$-$C_6$ alkyl). In addition, —($C_1$-$C_{10}$)alkylene- and —($C_1$-$C_{10}$)heteroalkylene can be substituted by one or more oxo groups (C=O) and the nitrogen and sulfur atoms of a heteroalkylene group can optionally be oxidized (e.g., to form S(O), —S(O)$_2$—, or N-oxide). Suitable heteroalkylene groups can include one or more 1,2-dioxyethylene units —(O—$CH_2CH_2$)$_n$O—, where n is an integer, e.g., 1, 2, 3, 4 or 5). The —($C_1$-$C_{10}$)alkylene- and —($C_1$-$C_{10}$)heteroalkylene also include —($C_1$-$C_6$)alkylene- and —($C_1$-$C_6$)heteroalkylene and —($C_1$-$C_3$)alkylene- and —($C_1$-$C_3$)heteroalkylene.

In some embodiments, the group of $L^2$ is one that can disintegrate to release the drug molecule upon hydrolysis of a bond between the amino acid or peptide moiety -$A_y$- and L2.

Alternatively, a Compound of the Invention containing a self-immolative Spacer unit can release --D without the need for a separate hydrolysis step. In this embodiment, —Y— is a PAB group that is linked to --W.sub.w-- via the amino nitrogen atom of the PAB group, and connected directly to -D via a carbonate, carbamate or ether group. Without being bound by theory, Scheme 2 depicts a possible mechanism of Drug release of a PAB group which is attached directly to --D via a carbamate or carbonate group. An example of such a group is a para-amino benzyl $L^2$ group of formula —NH-p-$C_6H_4$—$CH_2$— or —NH-p-$C_6H_4$—$CH_2$—OC(O) that can release drug via an elimination reaction.

In some embodiments, the linker can be of the following formula:

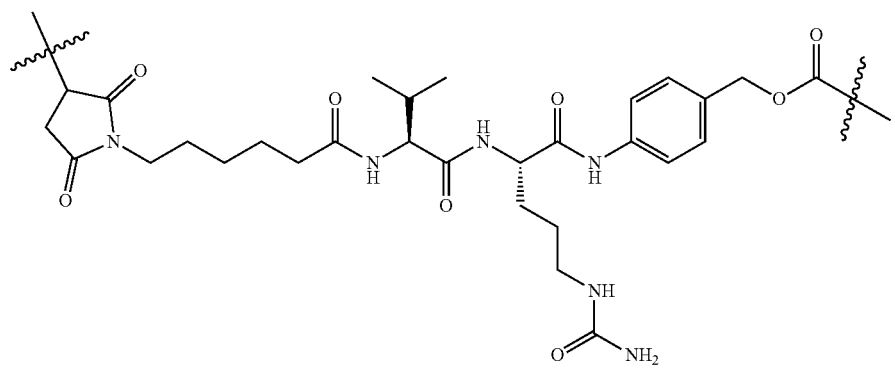 [SMILES: *C(=O)OCc1ccc(NC(=O)[C@H](CCCNC(N)=O)NC(=O)[C@@H](NC(=O)CCCCCN2C(=O)CC(*)C2=O)C(C)C)cc1]

or one of the following formulae (with an S or NH group forming the link between the antibody and linking group:

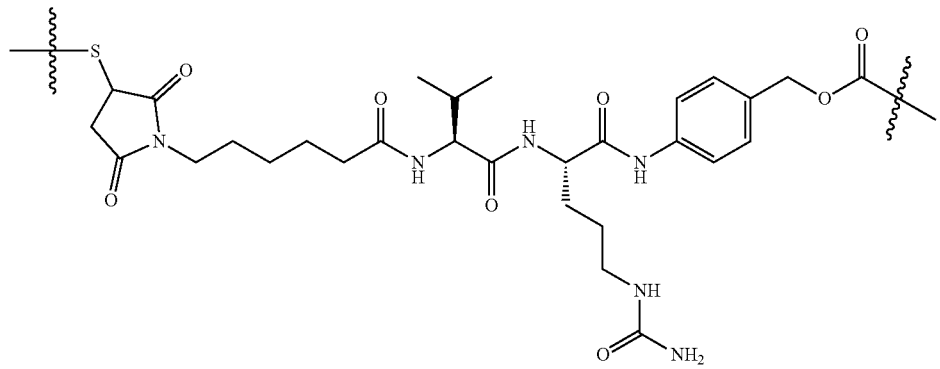

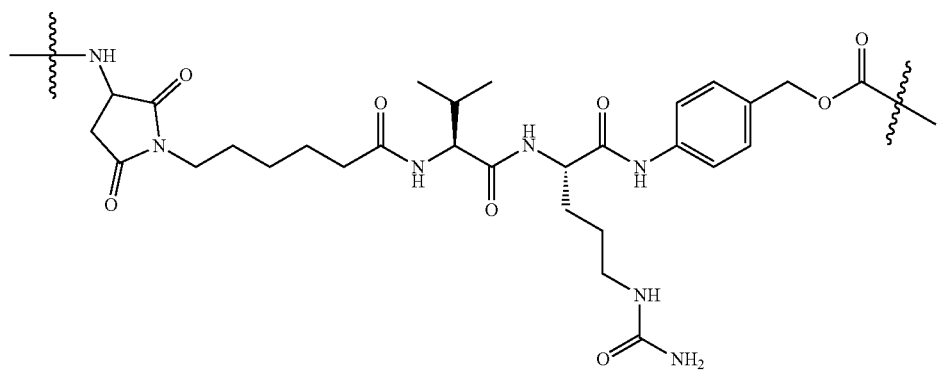

Figure 1:
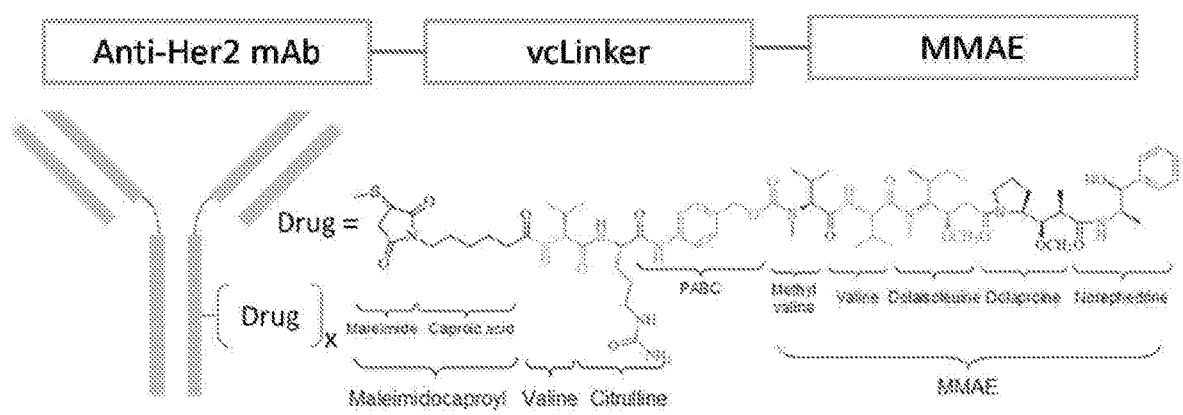
FIG. 1 contains a schematic of an MRG002 molecule having the anti-HER2 monoclonal antibody (MAB802), the vcLinker, and an auristatin derivative MMAE. X is the number of MMAE molecules conjugated per antibody.

In some cases, ADCs described herein (e.g., ADCs containing an anti-HER2 antibody and one or more anti-cancer drugs) can include a MAB802 antibody and about, on average, 3.8 molecules of MMAE linked by a vcLinker. For example, an ADC can be as described in Example 1. For example, an ADC can be as shown in FIG. 1.

ADCs

ADCs described herein (e.g., ADCs containing an anti-HER2 antibody and one or more anti-cancer drugs (e.g., MMAE)) can have decreased ADCC activity (e.g., relative to other anti-HER2 antibodies, such as anti-HER2 antibodies used in current FDA-approved HER2-targeted therapies (e.g., trastuzumab)). For example, ADCs described herein (e.g., ADCs containing an anti-HER2 antibody and one or more anti-cancer drugs (e.g., MMAE)) can have ADCC activity leading to decreased cell lysis. In some cases, an ADC can have ADCC activity leading to less than about 30% cell lysis (e.g., less than about 30%, less than about 29%, less than about 29%, less than about 28%, less than about 27%, less than about 26%, less than about 25%, less than about 24%, less than about 23%, less than about 22%, less than about 21%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, or less than about 5%). In some cases, an ADC can have ADCC activity leading to from about 0% to about 30% cell lysis (e.g., from about 0% to about 28%, from about 0% to about 25%, from about 0% to about 22%, from about 0% to about 20%, from about 0% to about 17%, from about 0% to about 15%, from about 0% to about 13%, from about 0% to about 10%, from about 0% to about 5%, from about 2% to about 30%, from about 5% to about 30%, from about 10% to about 30%, from about 12% to about 30%, from about 15% to about 30%, from about 18% to about 30%, from about 20% to about 30%, from about 22% to about 30%, from about 25% to about 30%, from about 1% to about 25%, from about 3% to about 22%, from about 5% to about 20%, from about 7% to about 18%, or from about 10% to about 13% cell lysis). For example, an ADC can have ADCC activity leading to from about 9.9% to about 12.7% cell lysis. For example, an ADC can have ADCC activity leading to about 11.3% cell lysis.

ADCs described herein (e.g., ADCs containing an anti-HER2 antibody and one or more anti-cancer drugs (e.g., MMAE)) can have decreased CD16 binding affinity (e.g., relative to other anti-HER2 antibodies, such as anti-HER2 antibodies used in current FDA-approved HER2-targeted therapies (e.g., trastuzumab)). The CD16 can be a human CD16. The CD16 can be a CD16a or a CD16b form of CD16. For example, the CD16 can be a CD16a. In some cases, the CD16 can have a valine residue at position 176 (e.g., a 176Val CD16). In some cases, the CD16 can have a phenylalanine residue at position 176 (e.g., a 176Phe CD16). In some cases, the CD16 can have a phenylalanine residue at position 176. In some cases, an ADC can have a CD16 binding affinity having a KD value of greater than about $2.5 \times 10^{-08}$ M (e.g., greater than about $2.7 \times 10^{-08}$ M, greater than about $3.0 \times 10^{-08}$ M, greater than about $3.2 \times 10^{-08}$ M, greater than about $3.5 \times 10^{-08}$ M, greater than about $4.0 \times 10^{-08}$ M, greater than about $4.3 \times 10^{-08}$ M, greater than about $4.5 \times 10^{-08}$ M, greater than about $4.8 \times 10^{-08}$ M, greater than about $5.0 \times 10^{-08}$ M, greater than about $5.3 \times 10^{-08}$ M, greater than about $5.5 \times 10^{-08}$ M, greater than about $5.7 \times 10^{-08}$ M, greater than about $6.0 \times 10^{-08}$ M, greater than about $6.2 \times 10^{-08}$ M, greater than about $6.5 \times 10^{-08}$ M, greater than about $6.8 \times 10^{-08}$ M, greater than about $2.5 \times 10^{-08}$ M, greater than about $7.0 \times 10^{-08}$ M, greater than about $7.3 \times 10^{-08}$ M, greater than about $7.5 \times 10^{-08}$ M, greater than about $7.8 \times 10^{-08}$ M, greater than about $8.0 \times 10^{-08}$ M, greater than about $8.2 \times 10^{-08}$ M, greater than about $8.5 \times 10^{-08}$ M, greater than about $8.7 \times 10^{-08}$ M, greater than about $9.0 \times 10^{-08}$ M, or greater than about $9.5 \times 10^{-08}$ M). In some cases, an ADC can have a CD16 binding affinity having a KD value of from about $2.5 \times 10^{-08}$ M to about $10.0 \times 10^{-08}$ M (e.g., from about $3.0 \times 10^{-08}$ M to about $10.0 \times 10^{-08}$ M, from about $3.5 \times 10^{-08}$ M to about $10.0 \times 10^{-08}$ M, from about $4.0 \times 10^{-08}$ M to about $10.0 \times 10^{-08}$ M, from about $4.5 \times 10^{-08}$ M to about $10.0 \times 10^{-08}$ M, from about $5.0 \times 10^{-08}$ M to about $10.0 \times 10^{-08}$ M, from about $5.5 \times 10^{-08}$ M to about $10.0 \times 10^{-08}$ M, from about $6.0 \times 10^{-08}$ M to about $10.0 \times 10^{-08}$ M, from about $6.5 \times 10^{-08}$ M to about $10.0 \times 10^{-08}$ M, from about $6.8 \times 10^{-08}$ M to about $10.0 \times 10^{-08}$ M, from about $7.0 \times 10^{-08}$ M to about $10.0 \times 10^{-08}$ M, from about $7.2 \times 10^{-08}$ M to about $10.0 \times 10^{-08}$ M, from about $7.5 \times 10^{-08}$ M to about $10.0 \times 10^{-08}$ M, from about $7.8 \times 10^{-08}$ M to about $10.0 \times 10^{-08}$ M, from about $8.0 \times 10^{-08}$ M to about $10.0 \times 10^{-08}$ M, from about $8.2 \times 10^{-08}$ M to about $10.0 \times 10^{-08}$ M, from about $8.5 \times 10^{-08}$ M to about $10.0 \times 10^{-08}$ M, from about $2.5 \times 10^{-08}$ M to about $9.5 \times 10^{-08}$ M, from about $2.5 \times 10^{-08}$ M to about $9.0 \times 10^{-08}$ M, from about $2.5 \times 10^{-08}$ M to about $8.8 \times 10^{-08}$ M, from about $2.5 \times 10^{-08}$ M to about $8.5 \times 10^{-08}$ M, from about $2.5 \times 10^{-08}$ M to about $8.2 \times 10^{-08}$ M, from about $2.5 \times 10^{-08}$ M to about $8.0 \times 10^{-08}$ M, from about $2.5 \times 10^{-08}$ M to about $7.7 \times 10^{-08}$ M, from about $2.5 \times 10^{-08}$ M to about $7.5 \times 10^{-08}$ M, from about $2.5 \times 10^{-08}$ M to about $7.3 \times 10^{-08}$ M, from about $2.5 \times 10^{-08}$ M to about $7.0 \times 10^{-08}$ M, from about $2.5 \times 10^{-08}$ M to about $6.8 \times 10^{-08}$ M, from about $2.5 \times 10^{-08}$ M to about $6.5 \times 10^{-08}$ M, from about $3.0 \times 10^{-08}$ M to about $9.8 \times 10^{-08}$ M, from about $3.5 \times 10^{-08}$ M to about $9.5 \times 10^{-08}$ M, from about $4.0 \times 10^{-08}$ M to about $9.2 \times 10^{-08}$ M, from about $4.5 \times 10^{-08}$ M to about $9.0 \times 10^{-08}$ M, from about $5.0 \times 10^{-08}$ M to about $8.8 \times 10^{-08}$ M, from about $5.5 \times 10^{-08}$ M to about $8.5 \times 10^{-08}$ M, from about $6.0 \times 10^{-08}$ M to about $8.2 \times 10^{-08}$ M, from about $6.5 \times 10^{-08}$ M to about $8.0 \times 10^{-08}$ M, or from about $6.8 \times 10^{-08}$ M to about $7.8 \times 10^{-08}$ M). For example, an ADC can have a CD16 binding affinity (e.g., a binding affinity for a human 176Val CD16a) having a KD value of about $8.094 \times 10^{-08}$ M to about $8.465 \times 10^{-08}$ M. For example, an ADC can have a CD16 binding affinity (e.g., a binding affinity for a human 176Phe CD16a) having a KD value of about $7.877 \times 10^{-07}$ M to about $9.708 \times 10^{-07}$ M.

ADCs described herein (e.g., ADCs containing an anti-HER2 antibody and one or more anti-cancer drugs (e.g., MMAE)) can have at least one (e.g., 1, 2, 3, 4, 5, 6, or more) molecule of an anti-cancer drug (e.g., per molecule of anti-HER2 antibody). In some cases, ADCs described herein can have more than one (e.g., 2, 3, 4, 5, 6, or more) molecule of an anti-cancer drug (e.g., per molecule of anti-HER2 antibody). For example, an ADC can have from about 3 molecules to about 8 molecules of MMAE (e.g., from about 3 molecules to about 7 molecules, from about 3 molecules to about 6 molecules, from about 3 molecules to about 5 molecules, from about 3 molecules to about 4 molecules, from about 4 molecules to about 8 molecules, from about 5 molecules to about 8 molecules, from about 6 molecules to about 8 molecules, from about 7 molecules to about 8 molecules, from about 4 molecules to about 7 molecules, from about 5 molecules to about 6, from about 4 molecules to about 5 molecules, or molecules from about 6 molecules to about 7 molecules of MMAE). For example, ADCs described herein can have about 3 to about 4 molecules of MMAE per molecule of MAB802. For example, ADCs described herein can have, on average, about 3.8 molecules of MMAE per molecule of MAB802. In some cases, ADCs described herein (e.g., ADCs containing an anti-HER2 antibody and one or more anti-cancer drugs (e.g., MMAE)) can have an increased DAR (e.g., relative to other HER2-targeted ADCs, such current FDA-approved HER2-targeted ADCs (e.g., T-DM1)). The DAR, as used herein, refers to the number of molecules of anti-cancer drug conjugated to an anti-HER2 antibody. It will be understood that ADCs described herein typically contain a whole number of molecules of anti-cancer drug, and that any DAR provided as a rational number (e.g., suggesting a fraction or portion of a molecule) is intended to refer an average number of molecules of anti-cancer drug per anti-HER2 antibody. In some cases, an ADC can have a DAR of greater than about 3.5 (e.g., greater than about 3.55, greater than about 3.6, greater than about 3.65, greater than about 3.7, greater than about 3.75, or greater than about 3.8). For example, an ADC can have a DAR of from about 3.5 to about 8 (e.g., from about 4 to about 8, from about 4.5 to about 8, from about 5 to about 8, from about 5.5 to about 8, from about 6 to about 8, from about 6.5 to about 8, from about 7 to about 8, from about 3.5 to about 7, from about 3.5 to about 6.5, from about 3.5 to about 6, from about 3.5 to about 5.5, from about 3.5 to about 5, from about 3.5 to about 4.5, from about 3.5 to about 4, from about 3.6 to about 7, from about 3.7 to about 6, or from about 3.8 to about 5). For example, an ADC can have a DAR of about 3.8.

In some cases, ADCs described herein (e.g., ADCs containing an anti-HER2 antibody and one or more anti-cancer drugs) can have ADCC activity leading to from about 9.9% to about 12.7% cell lysis (e.g., about 11.3% cell lysis), can have a CD16 binding affinity (e.g., a binding affinity for a human 176Val CD16a) having a KD value of about $8.094 \times 10^{-08}$ M to about $8.465 \times 10^{-08}$ M, can have a CD16 binding affinity (e.g., a binding affinity for a human 176Phe CD16a) having a KD value of about $7.877 \times 10^{-07}$ M to about $9.708 \times 10^{-07}$ M, and/or can have a DAR of about 3.8.

In some cases, ADCs described herein (e.g., ADCs containing an anti-HER2 antibody and one or more anti-cancer drugs) also can include one or more additional components. For example, ADCs can include detectable labels such as, without limitation, fluorescent labels (e.g., to monitor loca).

In some embodiments, the ADC can be represented by the following formula:

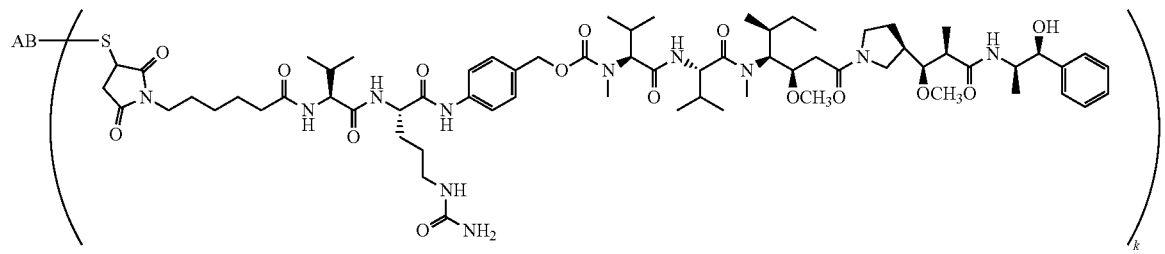

wherein AB represents the antibody and k represents the number of attached linker/drug groups per molecule of antibody. For any given antibody molecule, k represents an integer, such as 0, 1, 2, 3, 4, 5, 6, 7, 8, 9, or 10. For the ADC represented as a whole, k represents the drug/antibody ratio (i.e., the average number of drug molecules attached per antibody). In some embodiments, k can be in the range from about 1 to about 6, e.g., about 1, about 1.5, about 2, about 2.5, about 3, about 3.5, about 4, about 4.5, about 5, about 5.5, or about 6. In some embodiments, k can be about 3.5 or greater, e.g., about 3.55 or greater, about 3.6 or greater, about 3.7 or greater, about 3.75 or greater, or about 3.8 or greater.

Methods

This document also provides methods and materials for making and using ADCs described herein (e.g., ADCs containing an anti-HER2 antibody (e.g., MAB802) and one or more anti-cancer drugs). For example, an ADC containing an anti-HER2 antibody and one or more anti-cancer drugs can be administered to a mammal (e.g., a human) having a HER2-expressing cancer to treat the mammal.

As used herein, the terms "treat" or "treating" refer to one or more of (1) preventing a disease; e.g., preventing a disease, condition or disorder in an individual who may be predisposed to the disease, condition or disorder but does not yet experience or display the pathology or symptomatology of the disease; (2) inhibiting a disease; e.g., inhibiting a disease, condition or disorder in an individual who is experiencing or displaying the pathology or symptomatology of the disease, condition or disorder (i.e., arresting further development of the pathology and/or symptomatology); and (3) ameliorating a disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

In some cases, treating cancer can include reducing the number, frequency, or severity of one or more (e.g., two, three, four, or five) signs or symptoms of a cancer in a mammal having a cancer. For example, treatment can reduce the severity of a cancer (e.g., can reduce the number of cancer cells in and/or reduce the size (e.g., volume) of a tumor), reduce cancer progression (e.g., can reduce or eliminate tumor growth and/or metastasis or can reduce the proliferative, migratory, and/or invasive potential of cancer cells), and/or reduce the risk of re-occurrence of a cancer in a mammal having cancer. For example, administering one or more ADCs containing an anti-HER2 antibody (e.g., MAB802) and one or more anti-cancer drugs (e.g., MMAE) to a mammal (e.g., a human) having a HER2-expressing cancer can inhibit cancer cell growth of HER2-expressing cancer cells. For example, administering one or more ADCs containing an anti-HER2 antibody (e.g., MAB802) and one or more anti-cancer drugs (e.g., MMAE) to a mammal (e.g., a human) having a HER2-expressing cancer can reduce the tumor volume of a HER2-expressing tumor.

Any appropriate mammal having a HER2-expressing cancer can be treated as described herein. For example, humans and other primates such as monkeys having a HER2-expressing cancer can be treated with one or more ADCs described herein (e.g., ADCs containing an anti-HER2 antibody (e.g., MAB802) and one or more anti-cancer drugs) to reduce a symptom of the cancer, and/or to reduce the number of cancer cells present within the mammal within the human or other primate. In some cases, dogs, cats, horses, cows, pigs, sheep, mice, and rats having a HER2-expressing cancer can be treated with one or more ADCs containing an anti-HER2 antibody (e.g., MAB802) and one or more anti-cancer drugs as described herein.

When treating a mammal (e.g., a human) having a HER2-expressing cancer as described herein, the HER2-expressing cancer can be any appropriate HER2-expressing cancer. In some cases, a HER2-expressing cancer can be a refractory cancer (e.g., a cancer that is resistant (e.g., does not respond to) an anti-cancer drug). For example, a cancer treated as described herein can be a trastuzumab resistant cancer. For example, a cancer treated as described herein can be a T-DM1 resistant cancer. In some cases, a HER2-expressing cancer can be a relapsed (e.g., metastatic) cancer. Examples of HER2-expressing cancers that can be treated as described herein include, without limitation, breast cancers, gastric cancers, lung cancers, colon cancers, ovarian cancers, bladder cancers, cervical cancers, prostate cancers, thyroid cancers, head and neck carcinomas, glioblastomas, and sarcomas. For example, a HER2-expressing cancer can be a HER2-expressing breast cancer (e.g., a trastuzumab and/or T-DM1 resistant breast cancer). For example, a HER2-expressing cancer can be a HER2-expressing gastric cancer (e.g., a trastuzumab and/or T-DM1 resistant gastric cancer).

In some cases, a mammal having cancer can be assessed to determine if the cancer is a HER2-expressing cancer. Any appropriate method can be used to determine whether or not a cancer is a HER2-expressing cancer. For example, expression of HER2 can be determined using, for example, a transcription assay such as RT-PCR and/or a translation assay such as a western blot analysis.

Once identified as having a HER2-expressing cancer (e.g., a HER2-expressing cancer breast cancer or a HER2-expressing cancer gastric cancer), a mammal can be administered one or more ADCs described herein (e.g., ADCs containing an anti-HER2 antibody (e.g., MAB802) and one or more anti-cancer drugs).

One or more ADCs described herein (e.g., ADCs containing an anti-HER2 antibody (e.g., MAB802) and one or more anti-cancer drugs) can be administered to a mammal having a cancer as a combination therapy with one or more additional agents used to treat a cancer. For example, one or more ADCs described herein can be administered to a mammal in combination with one or more anti-cancer treatments (e.g., radiation therapy, chemotherapy, other targeted therapies, hormonal therapy, angiogenesis inhibitors, and/or immune checkpoint inhibitors such as anti-PD-1 antibodies, anti-PD-L1 antibodies, anti-CTLA4 antibodies, and anti-TIGIT antibodies). In cases where a composition including one or more ADCs described herein is used with additional agents treat a cancer, the one or more additional agents can be administered at the same time or independently. In some cases, a composition including one or more ADCs described herein can be administered first, and the one or more additional agents administered second, or vice versa.

Compositions and Administration

One or more ADCs described herein (e.g., ADCs containing an anti-HER2 antibody (e.g., MAB802) and one or more anti-cancer drugs) can be formulated into a composition (e.g., a pharmaceutically acceptable composition) for administration to a mammal having a HER2-expressing cancer. For example, a therapeutically effective amount of one or more ADCs described herein can be formulated into a composition and administered to a mammal having a HER2-expressing cancer to treat the mammal. A composition can be a sterile composition. A composition can be formulated for administration in any appropriate form including, without limitation, solutions, suspensions, sustained-release formulations, tablets, capsules, pills, powders, and granules.

A composition containing one or more ADCs described herein (e.g., ADCs containing an anti-HER2 antibody (e.g., MAB802) and one or more anti-cancer drugs) can include a plurality (e.g., 2, 3, 4, 5, 6, 7, 8, 9, 10, 11, 12, 15, 20, 25, 50, 75, 100, or more) of antibody-drug conjugates. In some cases, ADCs described herein within a composition containing a plurality of ADCs can contain the same number of molecules of one or more anti-cancer drugs. In some cases, ADCs described herein within a composition containing a plurality of ADCs can contain differing numbers of molecules of one or more anti-cancer drugs. In some cases, a composition can have an increased DAR (e.g., relative to other HER2-targeted ADCs, such current FDA-approved HER2-targeted ADCs (e.g., T-DM1)). In some cases, a composition can have a DAR of greater than about 3.5 (e.g., greater than about 3.55, greater than about 3.6, greater than about 3.65, greater than about 3.7, greater than about 3.75, or greater than about 3.8). For example, a composition can have a DAR of from about 3.5 to about 8 (e.g., from about 4 to about 8, from about 4.5 to about 8, from about 5 to about 8, from about 5.5 to about 8, from about 6 to about 8, from about 6.5 to about 8, from about 7 to about 8, from about 3.5 to about 7, from about 3.5 to about 6.5, from about 3.5 to about 6, from about 3.5 to about 5.5, from about 3.5 to about 5, from about 3.5 to about 4.5, from about 3.5 to about 4, from about 3.6 to about 7, from about 3.7 to about 6, or from about 3.8 to about 5). For example, an ADC can have a DAR of about 3.8.

In some cases, a composition containing one or more ADCs described herein (e.g., ADCs containing an anti-HER2 antibody (e.g., MAB802) and one or more anti-cancer drugs) can be a pharmaceutically acceptable composition. For example, a therapeutically effective amount of one or more ADCs described herein can be formulated into a pharmaceutically acceptable composition and administered to a mammal having a HER2-expressing cancer to treat the mammal. As used herein, the term "pharmaceutically acceptable" refers to compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. For example, a therapeutically effective amount of one or more T-type calcium channel antagonists can be formulated together with one or more pharmaceutically acceptable carriers (e.g., additives, diluents, and/or excipients). A pharmaceutically acceptable carrier can be a solid, semi-solid, or liquid material. A pharmaceutically acceptable carrier can be any compound which acts as a vehicle, carrier, or medium for one or more T-type calcium channel antagonists. Examples of pharmaceutically acceptable carriers that may be used in a pharmaceutically acceptable composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol such as Vitamin E TPGS, sodium carboxymethylcellulose, polyacrylates, waxes, polyethylene-polyoxypropylene-block polymers, and wool fat.

A composition (e.g., a pharmaceutical composition) containing one or more ADCs described herein (e.g., ADCs containing an anti-HER2 antibody (e.g., MAB802) and one or more anti-cancer drugs) can be formulated for administration in any appropriate form. A composition described herein can be in a solid form or liquid form. In some cases, a pharmaceutically acceptable composition containing one or more ADCs described herein can be a sustained-release composition. Examples of forms in which a composition described herein can be formulated include, without limitation, solutions, suspensions, tablets, capsules (e.g., soft gelatin capsules or hard gelatin capsules), pills, powders, granules, lozenges, sachets, cachets, elixirs, emulsions, syrups, aerosols (e.g., solid aerosols or liquid aerosols), and ointments. In some cases, a pharmaceutically acceptable composition containing one or more ADCs described herein can be a sterile composition. For example, a pharmaceutically acceptable composition containing one or more ADCs described herein can include aqueous and non-aqueous sterile injection solutions that can contain anti-oxidants, buffers, bacteriostats, and solutes that render the composition isotonic with the blood of the intended recipient; and aqueous and non-aqueous sterile suspensions that may include suspending agents and thickening agents.

A composition (e.g., a pharmaceutical composition) containing one or more ADCs described herein (e.g., ADCs containing an anti-HER2 antibody (e.g., MAB802) and one or more anti-cancer drugs) can be designed for any appropriate type of administration (e.g., topical, oral, parenteral, or inhaled administration). When being administered by topical administration, a pharmaceutical composition containing one or more ADCs described herein (e.g., ADCs containing an anti-HER2 antibody (e.g., MAB802) and one or more anti-cancer drugs) can be administered transdermally, epidermally, ophthalmically, and/or to mucous membranes (e.g., intranasally, vaginally, and rectally). When being administered by topical administration, a pharmaceutical composition containing one or more ADCs described herein can be in the form of, for example, transdermal patches, ointments, lotions, creams, gels, drops, suppositories, sprays, liquids and powders. When being administered by oral administration, a pharmaceutical composition containing one or more ADCs described herein (e.g., ADCs containing an anti-HER2 antibody (e.g., MAB802) and one or more anti-cancer drugs) can be in the form of, for example, a pill, tablet, or capsule. When being administered by parenteral administration, a pharmaceutical composition containing one or more ADCs described herein (e.g., ADCs containing an anti-HER2 antibody (e.g., MAB802) and one or more anti-cancer drugs) can be administered by intravenous, intraarterial, subcutaneous, intraperitoneal, intramuscular intracranial (e.g., intrathecal or intraventricular) injection or infusion. When being administered by parenteral administration, a pharmaceutical composition containing one or more ADCs described herein can be in the form of, for example, liquids, gels, drops, suppositories, sprays, and powders. When being administered by parenteral administration, a pharmaceutical composition containing one or more ADCs described herein can be administered in the form of a one or more bolus doses or may be administered by a continuous perfusion (e.g., by a pump). When being administered by inhaled administration, a pharmaceutical composition containing one or more ADCs described herein (e.g., ADCs containing an anti-HER2 antibody (e.g., MAB802) and one or more anti-cancer drugs) can be pulmonary. For example, administration of a pharmaceutical composition containing one or more ADCs described herein can include inhalation or insufflation of a liquid (e.g., an aerosol) and/or a solid (e.g., powder). When being administered by inhaled administration, a pharmaceutical composition containing one or more ADCs described herein can be in the form of, for example, liquids, gels, and powders.

A composition (e.g., a pharmaceutical composition) containing one or more ADCs described herein (e.g., ADCs containing an anti-HER2 antibody (e.g., MAB802) and one or more anti-cancer drugs) can be administered locally or systemically. For example, a composition containing one or more ADCs described herein can be administered systemically by an oral administration or by injection to a mammal (e.g., a human).

Effective doses of one or more ADCs described herein (e.g., ADCs containing an anti-HER2 antibody (e.g., MAB802) and one or more anti-cancer drugs) can vary depending on the severity of the cancer, the route of administration, the age and general health condition of the subject, excipient usage, the possibility of co-usage with other therapeutic treatments such as use of other agents, and the judgment of the treating physician.

An effective amount of a composition containing one or more ADCs described herein (e.g., ADCs containing an anti-HER2 antibody (e.g., MAB802) and one or more anti-cancer drugs) can be any amount that reduces the severity of a cancer, reduces cancer progression, and/or reduces the risk of re-occurrence of a cancer in the mammal without producing significant toxicity to the mammal. An effective amount of an ADC containing an anti-HER2 antibody (e.g., MAB802) and one or more anti-cancer drugs can be from about 0.6 mg per kg body weight (mg/kg) to about 10 mg/kg (e.g., from about 1 mg/kg to about 10 mg/kg, from about 2 mg/kg to about 10 mg/kg, from about 3 mg/kg to about 10 mg/kg, from about 4 mg/kg to about 10 mg/kg, from about 5 mg/kg to about 10 mg/kg, from about 6 mg/kg to about 10 mg/kg, from about 7 mg/kg to about 10 mg/kg, from about 8 mg/kg to about 10 mg/kg, from about 9 mg/kg to about 10 mg/kg, from about 0.6 mg/kg to about 9 mg/kg, from about 0.6 mg/kg to about 8 mg/kg, from about 0.6 mg/kg to about 7 mg/kg, from about 0.6 mg/kg to about 6 mg/kg, from about 0.6 mg/kg to about 5 mg/kg, from about 0.6 mg/kg to about 4 mg/kg, from about 0.6 mg/kg to about 3 mg/kg, from about 0.8 mg/kg to about 9 mg/kg, from about 1 mg/kg to about 8 mg/kg, from about 1.5 mg/kg to about 7 mg/kg, from about 2 mg/kg to about 6 mg/kg, from about 3 mg/kg to about 5 mg/kg, from about 1 mg/kg to about 4 mg/kg, from about 1.5 mg/kg to about 3 mg/kg, from about 2 mg/kg to about 4 mg/kg, or from about 2 mg/kg to about 6 mg/kg). For example, an effective amount of an ADC containing a MAB802 antibody and one or more molecules of MMAE can be from about 1.8 mg/kg to about 2.4 mg/kg. For example, an effective amount of an ADC containing a MAB802 antibody and one or more molecules of MMAE can be about 2 mg/kg. For example, an effective amount of an ADC containing a MAB802 antibody and one or more molecules of MMAE can be about 3 mg/kg. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., a cancer) may require an increase or decrease in the actual effective amount administered.

The frequency of administration of a composition containing one or more ADCs described herein (e.g., ADCs containing an anti-HER2 antibody (e.g., MAB802) and one or more anti-cancer drugs) can be any frequency that reduces the severity of a cancer, reduces cancer progression, and/or reduces the risk of re-occurrence of a cancer in the mammal without producing significant toxicity to the mammal. For example, the frequency of administration can be from about once a week to about once every four weeks, from about once every two weeks to about once every three weeks, or from about once every three weeks to about once every four weeks. In some cases, the frequency of administration can be about once every three weeks. The frequency of administration can remain constant or can be variable during the duration of treatment. A course of treatment with a composition containing one or more ADCs described herein can include rest periods. For example, a composition containing one or more ADCs described herein can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the cancer (e.g., a HER2-expressing cancer) may require an increase or decrease in administration frequency.

An effective duration for administering a composition containing one or more ADCs described herein (e.g., ADCs containing an anti-HER2 antibody (e.g., MAB802) and one or more anti-cancer drugs) can be any duration that reduces the severity of a cancer, reduces cancer progression, and/or reduces the risk of re-occurrence of a cancer in the mammal without producing significant toxicity to the mammal. For example, the effective duration can vary from several days to several weeks, months, or years. In some cases, the effective duration for the treatment of a cancer can range in duration from about one month to about 10 years. For example, the effective duration can include any appropriate number of administrations (e.g., cycles of treatment) of a composition containing one or more ADCs described herein. In some cases, the effective duration for the treatment of a cancer can include eight administrations (e.g., cycles of treatment) of a composition containing one or more ADCs described herein. Multiple factors can influence the actual effective duration used for a particular treatment. For example, an effective duration can vary with the frequency of administration, effective amount, use of multiple treatment agents, route of administration, and severity of the condition being treated.

In some cases, the cancer (e.g., a HER2-expressing cancer) present within a mammal can be monitored. For example, the size of a tumor present within a mammal, the number of cancer cells present within a mammal, and/or the severity of one or more symptoms related to the cancer being treated can be monitored. Any appropriate method can be used to determine whether or not the number of cancer cells present within a mammal is reduced. For example, imaging techniques can be used to assess the number of cancer cells present within a mammal.

A composition containing one or more ADCs described herein (e.g., ADCs containing an anti-HER2 antibody (e.g., MAB802) and one or more anti-cancer drugs) can be combined with packaging material and configured into a kit. The packaging material included in a kit can contain instructions or a label describing how the composition can be used to treat a mammal (e.g., a human) having a HER2-expressing cancer as described herein.

The invention will be further described in the following examples, which do not limit the scope of the invention described in the claims.

EXAMPLES

Example 1: Preparation of MRG002

Preparation of MAB802

MAB802 is a humanized recombinant IgG1 with an average expected molar mass at 145,423 Da. It was developed based on the same amino acid sequence as trastuzumab with elevated fucosylation (decreased afucosylation) and decreased ADCC activity according to the design of MRG002 molecule.

Light chain sequences (SEQ ID NO:4) and heavy chain sequences (SEQ ID NO:9) of MAB802 were encoded in expression plasmids and were expressed by CHO cells stably co-transfected with these plasmids. Subsequent subcloning by limiting dilution produced a cell line with relatively high specific productivity, good growth characteristics, and desired product quality, and was used to produce the primary cell bank (PCB), from which the master cell bank (MCB) and working cell bank (WCB) were derived.

The manufacturing of MAB802 was initiated by thawing a vial of the WCB containing CHO cells expressing the monoclonal antibody MAB802. Cells were serially expanded in vessels of increasing size until a 250 L production bioreactor. Cells were harvested and MAB802 was purified via three-step chromatography, followed by a nanofiltration step to remove any potential adventitious viral agents. The pool was then concentrated and buffer exchanged into a formulation buffer via an ultrafiltration/diafiltration step. The purified and formulated MAB802 bulk was filtered, filled into bottles, and stored.

The characterization of MAB802 included studies of the structural characteristics and physicochemical properties of the antibody, including primary, secondary and higher-order structure, post-translational modifications, in vitro bioactivity, purity and impurities.

The molecular weights of the intact antibody, the light chain and the heavy chain were in line with the theoretical value; the amino acid sequence was consistent with the theoretical sequence.

Posttranslational modifications were evaluated using glycosylation analysis procedures. Glycans were released from mAb by PNGase F, and were derivatized with fluorescent agent 2-AB. Derivatized glycans were analyzed with normal phase HPLC. Each glycan fraction was separated and quantitated by its peak area. A representative fluorescence chromatogram is shown in FIG. 2B. The posttranslational modifications were consistent among batches, and afucosylation was significantly lower than that of Herceptin® (Table 1).

TABLE 1.1

Percent N-glycan of MAB802 and Herceptin ®

| Type of N-glycan | Herceptin batch 1 | Herceptin batch 2 | Herceptin batch 3 | MAB802 batch 1 | MAB802 batch 2 | MAB802 batch 3 |
|---|---|---|---|---|---|---|
| G0F-GlcNAc | 1.04 | 0.78 | 0.71 | 0.43 | 0.49 | 0.43 |
| G0 | 5.18 | 5.05 | 5.1 | 0.3 | 0.29 | 0.29 |
| G0F | 40.9 | 38.98 | 36.92 | 52.43 | 53.44 | 50.52 |
| Man5 | 4.26 | 3.71 | 2.34 | 0.51 | 0.55 | 0.47 |
| G1 | 2.62 | 2.67 | 3.22 | 0.35 | 0.36 | 0.39 |
| G1F | 34.98 | 36.82 | 39.54 | 36.07 | 36.15 | 38.41 |
| G2F | 6.43 | 7.21 | 8.3 | 6.18 | 6.03 | 6.84 |
| Others | 4.59 | 4.78 | 3.87 | 3.73 | 2.69 | 2.65 |

TABLE 1.2

Comparison of afucosylation levels of MAB802 and Herceptin®

|  | MAB802 batch 1 | MAB802 batch 2 | MAB802 batch 3 | Herceptin batch 1 | Herceptin batch 2 | Herceptin batch 3 |
|---|---|---|---|---|---|---|
| Afucosylation % | 2.56 | 2.27 | 1.86 | 15.60 | 15.17 | 12.57 |

TABLE 1.3

Comparison of afucosylation levels of MAB802 and Herceptin®

|  | MAB802 | Herceptin® |
|---|---|---|
| Afucosylation (%)* | 2.23 | 14.45 |

Note:
*Average value from three batches

MAB802 showed significant lower ADCC activity than that of Herceptin® (FIG. 4), which is in agreement with lower CD16 binding affinity of MAB802 in comparison with Herceptin®.

Preparation of MRG002

MRG002 is an antibody drug conjugate (ADC) comprised of three components: the anti-HER2 monoclonal antibody (MAB802), the vcLinker, and an auristatin derivative MMAE (FIG. 1). Each MRG002 molecule carries, on average, 3.8 MMAE.

Approximately 10 mg of MAB802 antibody were buffer-exchanged into reducing buffer using diafiltration and the protein concentration was determined using $A_{280}$. The reductant DTT was added into the antibody at a molar ratio of 2:1 and the reaction mixture was incubated at room temperature for 2 hours with constant mixing. Then, partially reduced antibody was exchanged into a conjugation buffer with an 30 KD ultrafiltration device (15 mL in capacity) and the protein concentration was determined via $A_{280}$. 10 µL samples were applied to determine the average number of free thiol per antibody with Ellman's assay.

The following formula was used to calculate the molar concentration of free thiol:

$$C_{thiol} = \frac{A412 \times 11.2}{b \times 14150} (M)$$

where b is the optical path length of the cuvette (normally 1 cm).

The average number of free thiols per antibody was calculated based on the molar concentration of the antibody and free thiol.

A solution containing an drug-linker conjugate of MMAE linked via a valine-citrulline dipeptide (vcMMAE) was prepared in neat in DMSO was added into the reduced antibody at a molar ratio of 1:1 to free thiol, the composition was mixed and the resulting mixture was incubated for 30 minutes at room temperature with constant mixing. N-Acetyl-L-cysteine was added into the reaction mixture at a molar ratio of 20:1 to vcMMAE, the composition was mixed, and the resulting mixture was incubated for 5 minutes. At last, the mixture was purified and buffer-exchanged into a formulation buffer using a 30 KD ultrafiltration device (15 mL in capacity) to obtain the finished product, which was then stored at ≤−60° C.

Figure 3:
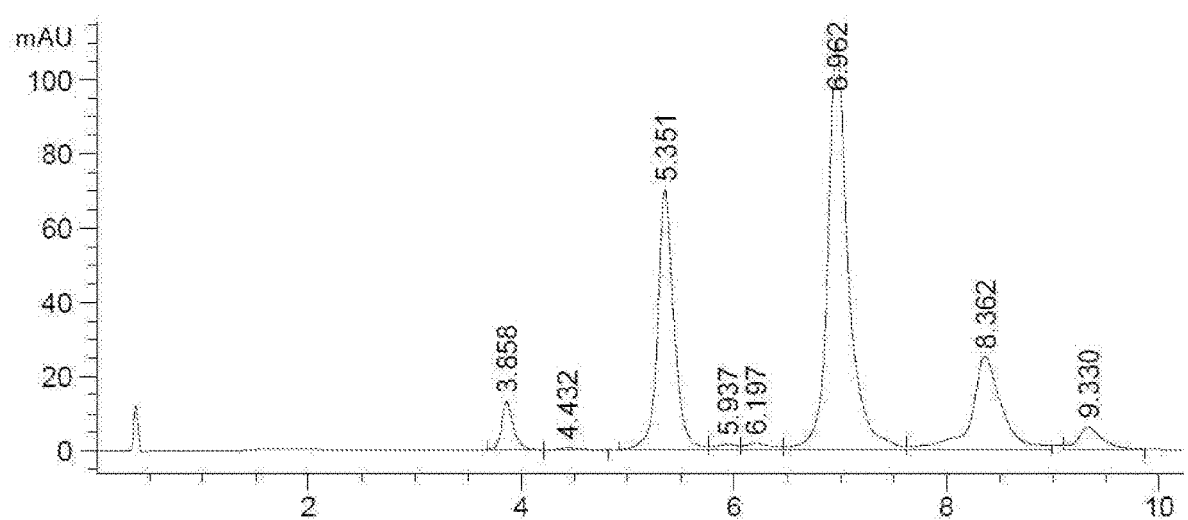
FIG. 3 contains a hydrophobic interaction chromatography-high performance liquid chromatography (HIC-HPLC) profile of MRG002.

Determination of Drug/Antibody Ratio:

The drug/antibody ratio (DAR) of prepared MRG002 batches was determined by HIC-HPLC profile (FIG. 3). HIC-HPLC was performed as described elsewhere (see, e.g., Ouyang, "Chapter 17: Drug-to-Antibody Ratio (DAR) and Drug Load Distribution by Hydrophobic Interaction Chromatography and Reversed Phase High-Performance Liquid Chromatography" 2013; Laurent Ducry (ed.), *Antibody-Drug Conjugates, Methods in Molecular Biology*, vol. 1045; Springer Science+Business Media).

Example 2: In Vitro Binding Affinity

Materials and Methods

The binding kinetics of MRG002, MAB802 and Herceptin® to immobilized HER2-Fc, Human CD16a (176Val, His Tag) and Human CD16a (176Phe, His Tag) were analyzed by surface plasmon resonance (SPR) using Biacore T200. Anti-his IgG and HER2-hFc were diluted to 20 µg/mL and 2 µg/mL, respectively, in sodium acetate (pH 4.5) and immobilized on Series S Sensor Chip CMS (GE Healthcare) by amine coupling to the amount of about 6000 and 300 resonance units, respectively; then for the flow cells with immobilized anti-his IgG, 0.5 µg/mL Human CD16a (176Val, His Tag) or Human CD16a (176Phe, His Tag) were injected at a flow rate of 10 µL/min to bind to the immobilized anti-his IgG. Finally, serial dilutions of MRG002, MAB802 or Herceptin® in HBS-EP buffer (10 mM HEPES, 150 mM NaCl, 3.0 mM EDTA, 0.05% surfactant P20, pH 7.4) were injected into their corresponding flow cell at a flow rate of 30 µL/min. The association rate (Ka), the dissociation rate (Kd) and the dissociation equilibrium constant (KD) were calculated using the BIAevaluation software (BIAcore) by fitting the data with bivalent binding model.

Experimental Results

In vitro binding affinity (hereinafter referred to as affinity) studies included the affinity of MRG002, MAB802 and reference drug Herceptin® to human HER2, as well as to human CD16a (176Val; 176Phe).

The affinity of MRG002 to human HER2, to human CD16a (176Val), and to human CD16a (176Phe) was studied. To compare the difference in affinity before and after conjugation, as well as the consistence among batches, 3 batches of MRG002 and the corresponding batches of MAB802 were studied. In addition, this study compared the affinity of Herceptin® with MRG002 and MAB802. The affinity was measured by Biacore T200 using surface plasmon resonance (SPR) technique as described elsewhere (see, e.g., Campbell et al., 2007 Biomaterials, 28(15):2380-2392).

The binding affinity of these samples to human HER2 antigen and to human CD16a are shown in Table 2.

TABLE 2

The binding affinity of MRG002, MAB802 and Herceptin ® to human HER2 antigen and human CD16a measured using Biacore

|  | Binding affinity to human HER2 antigen, KD (M) | Binding affinity to CD16a (176Val, His Tag), KD (M) | Binding affinity to CD16a (176Phe, His Tag), KD (M) |
| --- | --- | --- | --- |
| MRG002 | 6.625~7.503E-11 | 8.094~8.465E-08 | 7.877~9.708E-07 |
| MAB802 | 7.988~9.861E-11 | 6.988~7.089E-08 | 6.620~6.894E-07 |
| Herceptin ® | 1.219E-10 | 2.484E-08 | 2.535E-07 |

The binding affinity to human HER2 antigen: the KD value of the 3 batches of MRG002 ranged from $6.625 \times 10^{-11}$ to $7.503 \times 10^{-11}$ M; the KD value of the 2 batches of MAB802 ranged from $7.988 \times 10^{-H}$ to $9.861 \times 10^{-11}$ M; the KD value of Herceptin® was $1.219 \times 10^{-10}$ M. These results showed that the affinity were similar before and after conjugation, and that MAB802 has similar affinity as Herceptin®. The affinity of Herceptin® with human HER2 antigen was consistent with that reported in the literature (see, e.g., Selis et al., 2016 *International journal of molecular sciences*, 17(4):491).

The binding affinity to human CD16a (176Val, His Tag): the KD value of the 3 batches of MRG002 ranged from $8.094 \times 10^{-08}$ to $8.465 \times 10^{-08}$ M; the KD value of the 2 batches of MAB802 ranged from $6.988 \times 10^{-08}$ to $7.089 \times 10^{-08}$ M; the KD value of Herceptin® was $2.484 \times 10^{-08}$ M. These results showed that the affinity were similar before and after conjugation. However, MAB802's affinity was 3 times lower than Herceptin®.

The binding affinity to human CD16a (176Phe, His Tag): the KD value of the 3 batches of MRG002 ranged from $7.877 \times 10^{-07}$ to $9.708 \times 10^{-07}$ M; the KD value of the 2 batches of MAB802 ranged from $6.620 \times 10^{-07}$ to $6.894 \times 10^{-07}$ M; the KD value of Herceptin® was $2.535 \times 10^{-07}$ M. These results showed that the affinity were similar before and after conjugation. However, MAB802's affinity was 3 times lower than Herceptin®.

Example 3: ADCC/CDC Activity

Materials and Methods

MRG002 was prepared by conjugating recombinant humanized anti-HER2 IgG1 monoclonal antibody MAB802 to the linker-drug vcMMAE. In order to assess whether MRG002 retained the ADCC and CDC activity from MAB802 (which is a IgG1 type of monoclonal antibody), 3 batches of MRG002 and their corresponding MAB802 batches were tested for these activities.

Experimental Results

Figure 4:
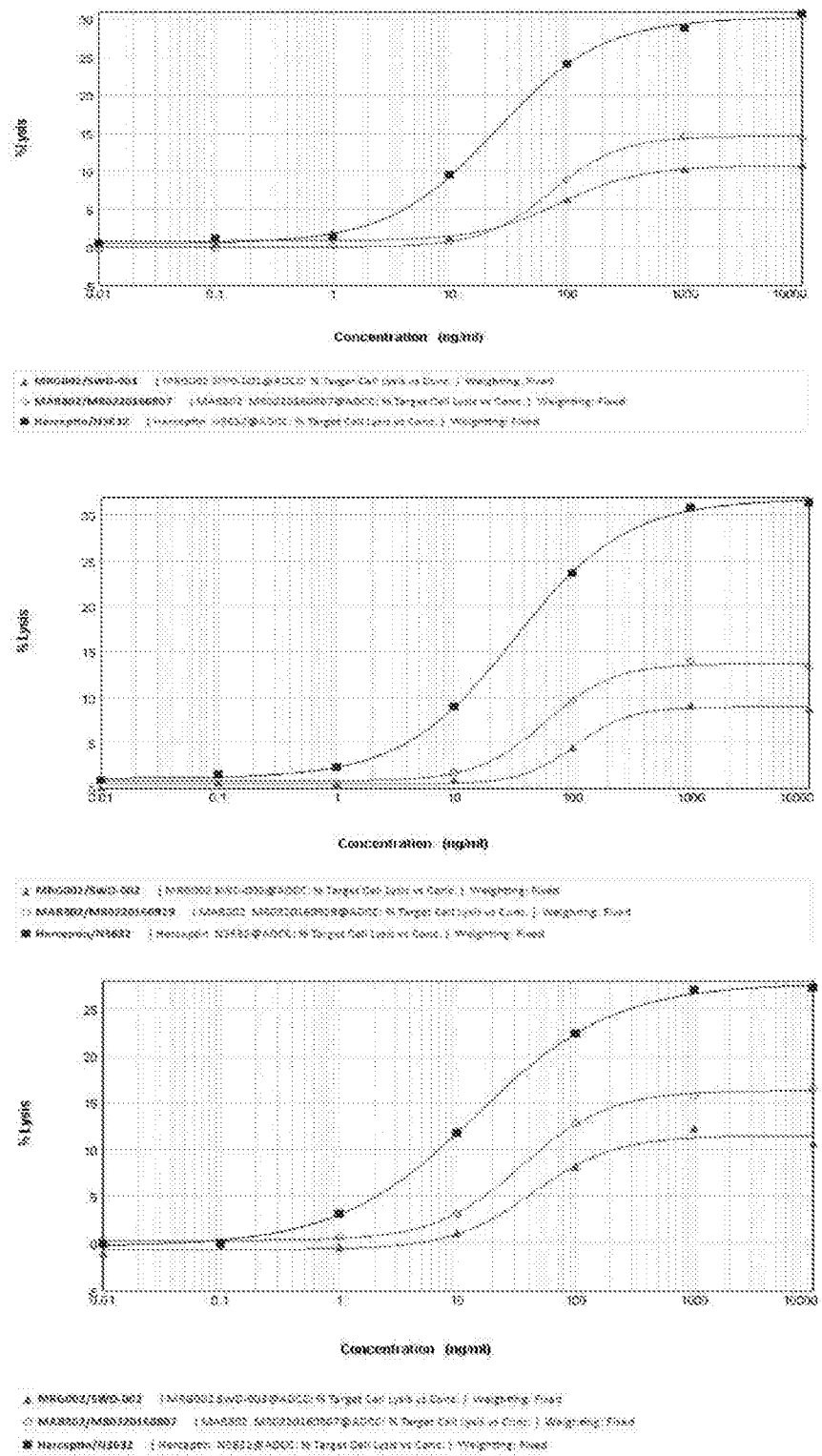
FIG. 4 contains graphs showing representative dose-response curves of MRG002, MAB802, and trastuzumab in an antibody-dependent cell-mediated cytotoxicity (ADCC) activity assay.

Using an engineered NK cell line as effector cells, SKBR3 cell line with high expression of HER2 as target cells, and Herceptin® as positive reference drug, ADCC activity was evaluated by calculating and comparing the amount of targeted cell lysis (Max % Target Cell Lysis). The experimental results are shown in FIG. 4.

The results showed that for the 3 batches of MRG002, the average amount of targeted cell lysis ranged from 9.9% to 12.7%, and the mean value was 11.3%; for the 2 batches of MAB802, the average amount of targeted cell lysis ranged from 13.9% to 15.7%, and the mean value was 14.8%; for Herceptin®, the average amount of targeted cell lysis ranged from 23.94% to 33.07%, and the mean value was 29.49%. These results showed that the ADCC activity of MRG002 was similar to that of MAB802 without drug conjugation, but was significantly lower than that of Herceptin®. Since the ADCC activity of antibody positively correlates with its affinity to CD16, lower ADCC activity of MRG002 and MAB802 compared with Herceptin® can be explained by reduced affinity to CD16 (see Table 2). The amount of targeted cell lysis for Herceptin® was consistent with previous report (see, e.g., Zhao et al., 2011 Proceedings of the National Academy of Sciences, 108(45): 18342-18347).

Using 20% normal human serum (NHS) as the source of complement, and HER2 overexpressing SKBR3 cells as target cells, CDC activity was determined by measuring the amount of ATP released into the culture medium by the target cells. The CDC activity of Rituxan® on Ramos cells was used as a positive control, and Herceptin® was used as the reference drug for MAB802.

The results showed that the CDC activity of Rituxan® on Ramos cells was very apparent, with targeted cell lysis of 100%. However, three batches of MRG002, three batches of MAB802 and Herceptin® did not show CDC activity on SKRB3 cells. The result that Herceptin® has no significant CDC activity on SKRB-3 cells is consistent with literature (see, e.g., Mamidi et al., 2013 *Molecular oncology*, 7(3): 580-594; Petricevic et al., 2013 *Journal of translational medicine*, 11(1):307; and Haen et al., 2016 *Oncotarget*, 7(11):13013).

Example 4: In Vitro Cytotoxicity Assay

Materials and Methods

Cells were thawed and passaged for two generations. After removal of the culture medium, cells were washed once with 5 mL DPBS, digested with 3 mL trypsin, washed and resuspended with the culture medium. 0.5 mL of the cell suspension was used for cell counting. After cell counting, the cells were plated in 96-well plates at the density of 8000 cells/well for SKBR3 cells, 20000 cells/well for BT-474 cells, 20000 cells/well for NCI-N87 cells, 24000 cells/well for MDA-MB-453 cells. After 24 hours incubation at 37° C., serially-diluted T-DM1 and MRG002 were added and incubated with cells for 96 hours, 20 μL/well CCK-8 color developing reagent was added, and finally $OD_{450\text{-}650}$ were read by a spectrometer and four parameter fitting of the readout were performed.

Reagents and sources are listed in Table 3 and Table 4, respectively.

TABLE 3

| Test article | | | | |
| --- | --- | --- | --- | --- |
| Name | Concentration | Manufacturer | Lot No. | Storage |
| MRG002 | 5.2 mg/mL | Shanghai Miracogen Inc. | SWD-001 | ≤-60° C. |
| T-DM1 | 10.3 mg/mL | Roche | N-1025 | ≤-60° C. |

TABLE 4

Cell line and culture medium

| Cell line name | Cancer Type | Her2 expression level | Origin | Culture medium |
|---|---|---|---|---|
| SKBR3 | Breast cancer | high | ATCC | McCoy's 5A + 10% FBS |
| BT-474 | Breast cancer | high | Shanghai Institute for Biological Sciences, CAS | RPMI1640 + 10% FBS |
| MDA-MB-453 | Breast cancer | medium | Shanghai Institute for Biological Sciences, CAS | L-15 + 10% FBS |
| NCI-N87 | Gastric cancer | high | Medicilon | RPMI1640 + 10% FBS |

Note:
Medicilon = Shanghai Medicilon Inc.

Results

Figure 5:
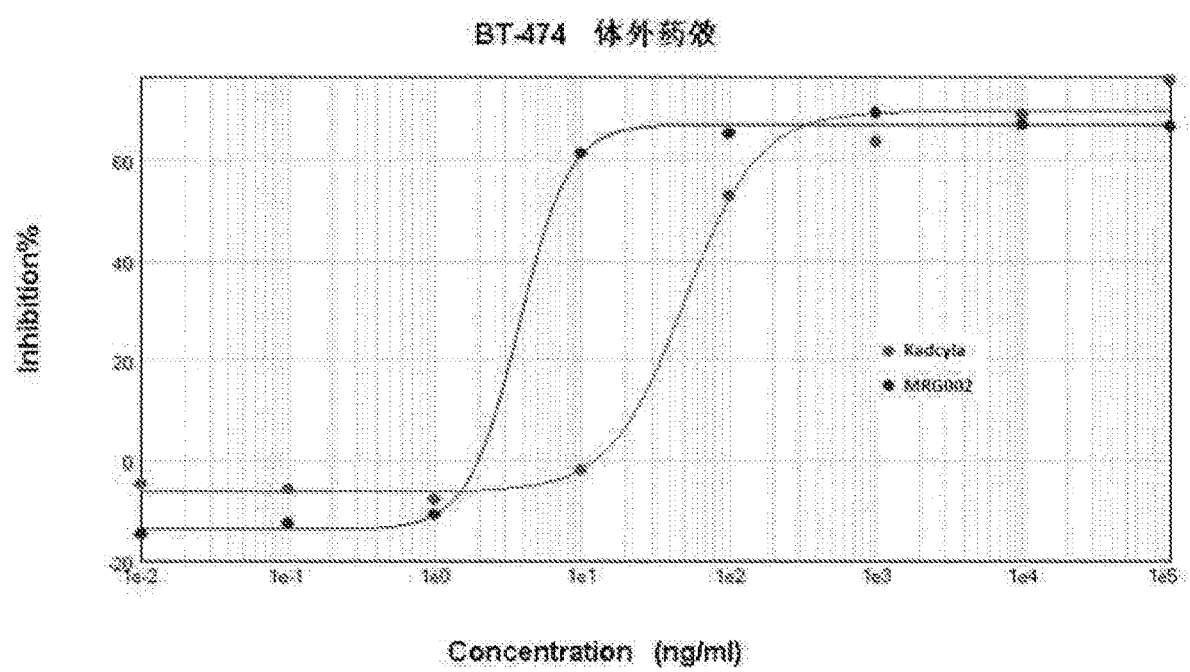
FIG. 5 contains a graph showing anti-proliferation activity of MRG002 and T-DM1 (Kadcyla®) in BT-474 cells.

Average $IC_{50}$ of MRG002 and T-DM1 are listed in Table 5, while representative in vitro cell growth inhibition curves are shown in FIG. 5.

TABLE 5

Anti-Proliferation Activity of MRG002 and T-DM1 in different cell lines

| Cell line | Type of tumor | Avg. $IC_{50}$ of MRG002 (ng/mL) | Avg. $IC_{50}$ of T-DM1 (ng/mL) | Fold of Activity |
|---|---|---|---|---|
| SKBR3 | Breast cancer | 1.8 ± 0.8 | 4.7 ± 1.3 | 2.6 |
| BT-474 | Breast cancer | 5.3 ± 3.5 | 136.5 ± 82.0 | 25.7 |
| MDA-MB-453 | Breast cancer | 59.9 ± 8.9 | 65.9 ± 8.5 | 1.1 |
| NCI-N87 | Gastric cancer | 22.7 ± 8.8 | 121.2 ± 19.9 | 5.3 |

Note:
Fold of Activity = Ratio of Avg. $IC_{50}$ of T-DM1 to Avg. $IC_{50}$ of MRG002

Table 5 shows that MRG002 was more effective than T-DM1 in inhibiting the growth of these cancer cells. For instance, MRG002 was 25-fold more potent in killing BT-474 breast cancer cells and 5.3-fold more potent in killing NCI-N87 gastric cancer cell line.

Example 5: In Vivo Efficacy Study

Materials and Methods

The anti-tumor activity of MRG002 was evaluated in two CDX (Cell line-Derived Xenograft) and a number of PDX (Patient-Derived Xenograft) models. The two CDX models were established with a breast cancer cell line BT-474 and a gastric cancer cell line NCI-N87, both of which have high level of HER2 expression, whereas PDX models exhibit varying levels of HER2 expression.

CDX models were established by subcutaneous inoculation of ~5×10⁶ BT-474 or NCI-N87 cells into BALB/c nude mice. Mice with BT-474 implantation received β-estradiol in the form of pellets placed subcutaneously to promote tumor growth. MRG002, T-DM1 or non-binding control ADCs were administered intravenously in a q7d×2, q7d×3 or q7d×4 regimen when tumors grew to a size of ~150 mm³~250 mm³.

PDX models were established by subcutaneous implantation of small fragments of human breast cancer or gastric cancer tissues (15-30 mm³) in BALB/c nude mice. Three days before implantation, mice intended for breast cancer xenografts received β-estradiol in the form of pellets placed subcutaneously to promote tumor growth. MRG002, T-DM1 or non-binding control ADC were administrated q3w×4 intravenously when tumors grew to a size of ~150 mm³ to ~250 mm³.

The PDX models consist of a number of gastric and breast cancer models, and many of these models are Herceptin®-resistant. In all these experiments, the commercially available HER2-targeting ADC drug T-DM1 (Kadcyla®) was used as a reference drug to compare anti-tumor activity.

Tumor sizes were measured twice per week throughout the study. The following formula was used to calculate tumor size: tumor volume (TV)=tumor length (1)×tumor width (w)²/2, where "1" and "w" represents the length and width of a tumor, respectively; relative tumor volume (RTV)=Vf/V0, where V0 is the tumor volume measured before grouping (i.e., Day 0) and Vf is the tumor volume measured on the last day of experiment; T/C (%)=(RTV of test article group/RTV of vehicle group)×100%; TGI %=(average TV of vehicle group−average TV of test article group)/average TV of test article group×100%. All animal experiments were carried out with approved institutional animal care and facility protocols.

Exploratory studies were carried out in BT-474 and NCI-N87 CDX models initially with information listed in Table 6.

TABLE 6

Information of the 2 CDX models used in in vivo efficacy studies

| Tumor type | Cell line | HER2 expression |
|---|---|---|
| Ductal breast cancer | BT-474 | High |
| Gastric cancer | NCI-N87 | High |

Results

In Vivo Efficacy in Breast and Gastric Cancer CDX Models

Figure 6:
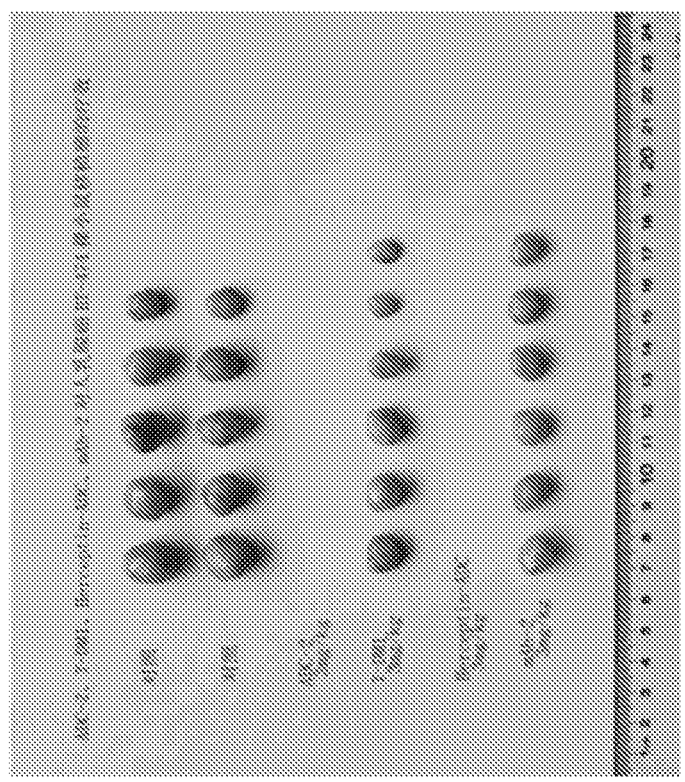
FIG. 6 shows the effect of MRG002, T-DM1, mAb-2 and trastuzumab-ADC on the tumor volume of BT-474 breast cancer CDX models (left) and the photo of tumors at the end of the study (right). ADC-2 represents MRG002; mAb-2 represents MAB802; trastuzumab-ADC is an ADC comprised of trastuzumab and vcMMAE, same as in MRG002; "对照" represents Vehicle; the number of animals was 10 for the vehicle group, and was 6 for other groups.
Figure 6:
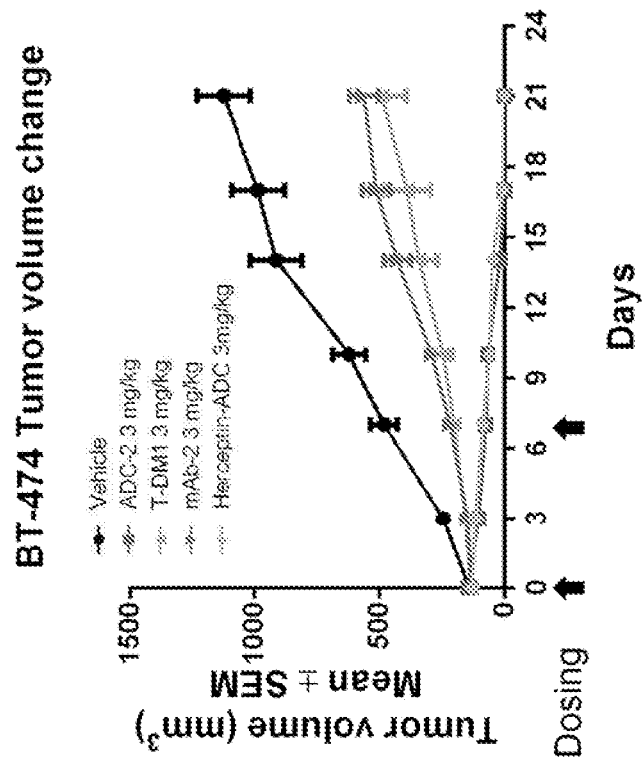

MRG002's anti-tumor activity in BT-474 breast cancer CDX model FIG. 6 showed that both MRG002 (3 mg/kg, iv, q7d×2) and Herceptin-ADC (3 mg/kg, iv, q7d×2) caused complete tumor regression at D21 in 6/6 mice. Meanwhile, T-DM1 (3 mg/kg, iv, q7d×2) and mAb-2 (3 mg/kg, iv, q7d×2) had tumor inhibition rate of 64% and 57% at D21, respectively. All test articles were well tolerated by the tumor-bearing mice.

MRG002's Anti-Tumor Activity in NCI-N87 Gastric Cancer CDX Model

Figure 7:
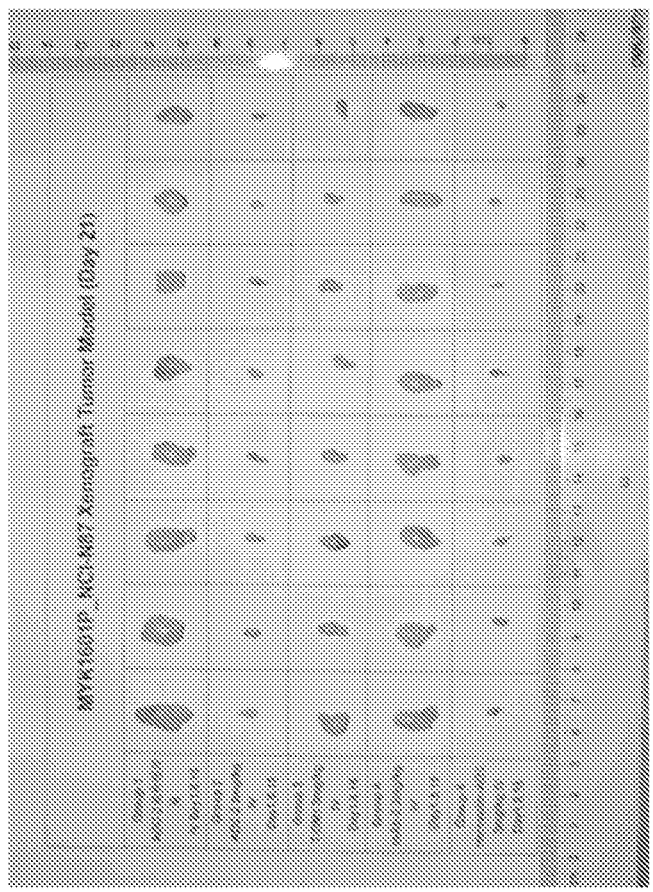
FIG. 7 shows the effect of MRG002, T-DM1, mAb-2 and trastuzumab-ADC on the tumor volume of NCI-N87 gastric cancer CDX models (left) and the photo of tumors at the end of the study (right). ADC-2 represents MRG002; mAb-2 represents MAB802; trastuzumab-ADC is an ADC comprised of trastuzumab and vcMMAE.
Figure 7:
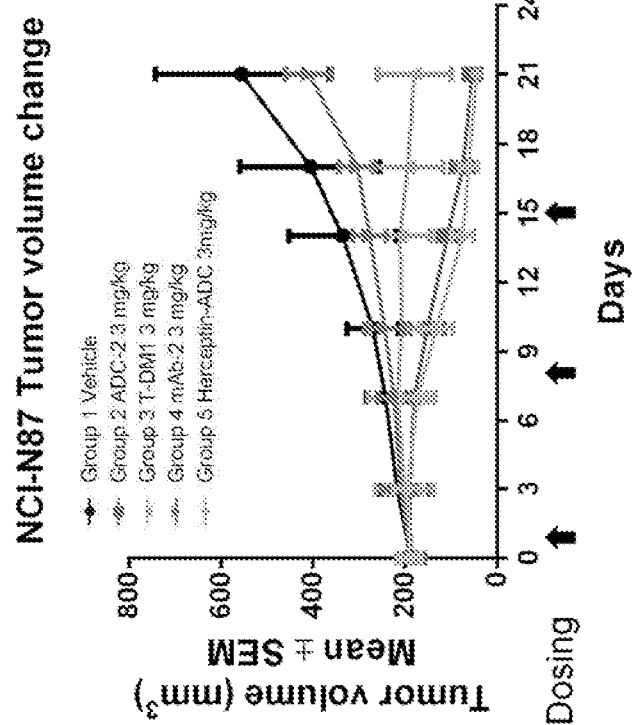

The anti-tumor activity of MRG002 in an exploratory study is shown in FIG. 7. MRG002 (3 mg/kg, iv, q7d×3) significantly inhibited the growth of HER2-high-expressing NCI-N87 xenografts, with T/C (%)=10.00% and TGI %=90.07%. The T/C (%) and TGI % of T-DM1 (3 mg/kg, iv, q7d×3) were 31.72% and 67.52%, respectively. The T/C (%) and TGI % of Herceptin-ADC (3 mg/kg, iv, q7d×3) were 8.28% and 91.86%, respectively. The T/C (%) and TGI % of mAb-2 (3 mg/kg, iv, q7d×3) were 74.83% and 26.28%, respectively. All test articles were tolerated by the tumor-bearing mice.

In Vivo Efficacy in Breast and Gastric Cancer PDX Models
MRG002's Anti-Tumor Activity in Breast Cancer PDX Model BC #046.

Figure 8:
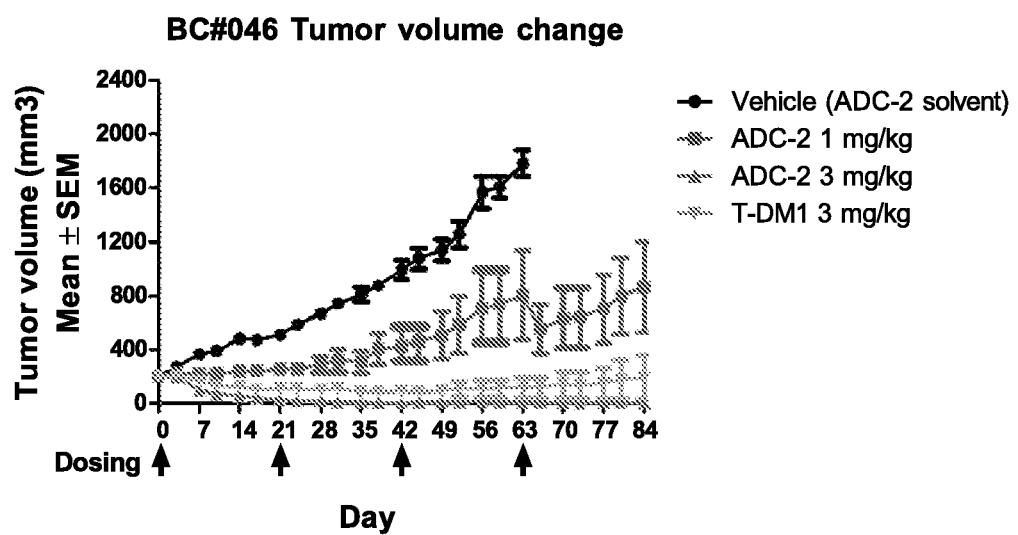
FIG. 8 shows the effect of MRG002 (ADC-2) and T-DM1 on the tumor volume of breast cancer PDX model BC #046.

BC #046 is a Herceptin®-resistant human breast cancer PDX model. The results (FIG. 8) showed that at Day 63, the T/C (%) for the MRG002 dose groups were 45.07% (P<0.001) at 1 mg/kg and 0.45% (P<0.001) at 3 mg/kg, while their corresponding TGI % were 54.93% and 99.55% the T/C (%) and TGI % of T-DM1 at 3 mg/kg were 6.56% (P<0.001) and 93.44%, respectively.

These results demonstrated that for the HER2-overexpressing human PDX model BC #046, both MRG002 and T-DM1 at 3 mg/kg were effective in inhibiting tumor growth, with MRG002 more potent than T-DM1 at the same dose level. All tumor-bearing mice tolerated MRG002 and T-DM1 well.

MRG002's Anti-Tumor Effect in Breast Cancer PDX Model BC #197

BC #197 is a Herceptin®-resistant human breast cancer PDX model. The results (FIG. 9) showed that at Day 69, the T/C (%) for the MRG002 groups were 14.11% (P<0.001) at 3 mg/kg and 2.26% (P<0.001) at 10 mg/kg, while their corresponding TGI % were 85.89% and 97.74%, with ⅛ and ⅝ complete tumor regression, as well as ⅛ and ⅜ partial tumor regression, respectively; the T/C (%) and TGI % of T-DM1 at 10 mg/kg were 63.31% (P<0.001) and 36.69%, respectively.

These results demonstrated that for the HER2-overexpressing PDX model BC #197, MRG002 effectively inhibited the tumor growth at both 3 mg/kg and 10 mg/kg, while T-DM1 at 10 mg/kg showed no much inhibition in tumor growth. All tumor-bearing mice tolerated MRG002 and T-DM1 well.

MRG002's Anti-Tumor Effect in Gastric Cancer PDX Model STO #041

STO #041 is a Herceptin®-resistant human gastric cancer PDX model. The results (FIG. 10) showed that at Day 46, the T/C (%) for the MRG002 dose groups were 61.46% (P<0.001) at 1 mg/kg and 32.47% (P<0.001) at 3 mg/kg, while their corresponding TGI % were 38.54% and 67.53%, respectively; the T/C (%) and TGI % of T-DM1 at 3 mg/kg were 83.66% (P>0.05) and 16.34%, respectively.

These results demonstrated that for the HER2-overexpressing human PDX model STO #041, only MRG002 at 3 mg/kg showed significant tumor inhibition. All tumor-bearing mice tolerated MRG002 and T-DM1 well.

MRG002's Anti-Tumor Effect in Gastric Cancer PDX Model STO #053

The results (FIG. 11) showed that at Day 45, the T/C (%) for the MRG002 dose groups were 47.75% (P<0.01) at 3 mg/kg and 0.65% (P<0.001) at 10 mg/kg, while their corresponding TGI % were 52.25% and 99.35%, respectively; the T/C (%) and TGI % of T-DM1 at 10 mg/kg were 19.43% (P>0.05) and 80.57%, respectively.

These results demonstrated that for the HER2-overexpressing human PDX model STO #053, both MRG002 at 3 mg/kg and T-DM1 at 10 mg/kg showed significant inhibition in tumor growth, while MRG002 at 3 mg/kg showed no much inhibition in tumor growth. In addition, all tumor-bearing mice tolerated MRG002 and T-DM1 well.

MRG002's Anti-Tumor Effect in Gastric Cancer PDX Model STO #069

The results (FIG. 12) showed that at Day 40, the T/C (%) for the MRG002 dose groups were 70.78% (P>0.05) at 1 mg/kg and 6.02% (P<0.001) at 3 mg/kg, while their corresponding TGI % were 29.22% and 93.98%, respectively; the T/C (%) and TGI % of T-DM1 at 3 mg/kg were 90.03% (P>0.05) and 9.97%, respectively.

These results demonstrated that for the HER2-overexpressing human PDX model STO #069, only MRG002 at 3 mg/kg showed significant tumor inhibition. All tumor-bearing mice tolerated MRG002 and T-DM1 well.

MRG002's Anti-Tumor Effect in Gastric Cancer PDX Model STO #179

STO #179 is a Herceptin®-resistant human gastric cancer PDX model. The results (FIG. 13) showed that at Day 59, the T/C (%) for the MRG002 dose groups were 35.20% (P<0.001) at 1 mg/kg and 4.14% (P<0.001) at 3 mg/kg, while their corresponding TGI % were 64.80% and 95.86%, respectively; the T/C (%) and TGI % of T-DM1 at 3 mg/kg were 92.56% (P>0.05) and 7.44%, respectively.

These results demonstrated that for the HER2-overexpressing human PDX model STO #179, MRG002 at both 1 mg/kg and 3 mg/kg exhibited significant anti-tumor activity in a dose-dependent manner, while T-DM1 at 3 mg/kg showed no significant tumor growth inhibition. All tumor-bearing mice tolerated MRG002 and T-DM1 well.

MRG002's Anti-Tumor Effect in Gastric Cancer PDX Model STO #240

STO #240 is a Herceptin®-resistant human gastric cancer PDX model. The results (FIG. 14) showed that at Day 83, the T/C (%) for the MRG002 dose groups were 20.70% (P<0.001) at 3 mg/kg and 18.78% (P<0.001) at 10 mg/kg, while their corresponding TGI % were 79.30% and 81.22%, respectively; the T/C (%) and TGI % of T-DM1 at 10 mg/kg were 40.96% (P<0.01) and 59.04%, respectively.

These results demonstrated that for the HER2-overexpressing human PDX model STO #240, MRG002 at both 3 mg/kg and 10 mg/kg showed significant anti-tumor activity, while T-DM1 at 10 mg/kg showed no significant tumor growth inhibition. All tumor-bearing mice tolerated MRG002 and T-DM1 well.

MRG002's Anti-Tumor Effect in Gastric Cancer PDX Model STO #410

STO #410 is a Herceptin®-resistant human gastric cancer PDX model. The results (FIG. 15) showed that at Day 38, the T/C (%) for the MRG002 dose groups were 39.94% (P<0.001) at 3 mg/kg and 0% (P<0.001) at 10 mg/kg, while their corresponding TGI % were 60.06% and 100%, respectively; the T/C (%) and TGI % of T-DM1 at 10 mg/kg were 108.79% (P>0.05) and −8.79%, respectively.

These results demonstrated that for the HER2-overexpressing human PDX model STO #410, MRG002 showed significant anti-tumor activity both at 3 mg/kg and 10 mg/kg, while T-DM1 at 10 mg/kg showed no inhibition in tumor growth. All tumor-bearing mice tolerated MRG002 and T-DM1 well.

Summary

The anti-tumor activity of these models are summarized in Table 7.

TABLE 7

In vivo efficacy of MRG002 (i.v., q3w × 4) in HER2-positive PDX models of gastric (STO) and breast cancer (BC).

| Model number | Test article | Dose (mg/kg) | Date for T/C (%) and TGI % calculation | T/C(%) | TGI % |
| --- | --- | --- | --- | --- | --- |
| BC#046 | Vehicle | / | Day 63 | 100 | 0 |
|  | MRG002 | 1 |  | 45.07 (P < 0.001) | 54.93 |
|  |  | 3 |  | 0.45 (P < 0.001) | 99.55 |
|  | T-DM1 | 3 |  | 6.56 (P < 0.001) | 93.44 |
| BC#197 | Vehicle | / | Day 69 | 100 | 0 |
|  | MRG002 | 3 |  | 14.11 (P < 0.001) | 85.89 |
|  |  | 10 |  | 2.26 (P < 0.001) | 97.74 |
|  | T-DM1 | 10 |  | 63.31 (P < 0.001) | 36.69 |
| STO#041 | Vehicle | / | Day 46 | 100 | 0 |
|  | MRG002 | 1 |  | 61.46 (P > 0.05) | 38.54 |
|  |  | 3 |  | 32.47 (P < 0.001) | 67.53 |
|  | T-DM1 | 3 |  | 83.66 (P > 0.05) | 16.34 |

TABLE 7-continued

In vivo efficacy of MRG002 (i.v., q3w × 4) in HER2-positive PDX models of gastric (STO) and breast cancer (BC).

| Model number | Test article | Dose (mg/kg) | Date for T/C (%) and TGI % calculation | T/C(%) | TGI % |
|---|---|---|---|---|---|
| STO#053 | Vehicle | / | Day 45 | 100 | 0 |
|  | MRG002 | 3 |  | 47.75 (P < 0.01) | 52.25 |
|  |  | 10 |  | 0.65 (P < 0.001) | 99.35 |
|  | T-DM1 | 10 |  | 19.43 (P < 0.001) | 80.57 |
| STO#069 | Vehicle | / | Day 40 | 100 | 0 |
|  | MRG002 | 1 |  | 70.78 (P > 0.05) | 29.22 |
|  |  | 3 |  | 6.02 (P < 0.001) | 93.98 |
|  | T-DM1 | 3 |  | 90.03 (P > 0.05) | 9.97 |
| STO#179 | Vehicle | / | Day 59 | 100 | 0 |
|  | MRG002 | 1 |  | 35.20 (P < 0.001) | 64.80 |
|  |  | 3 |  | 4.14 (P < 0.001) | 95.86 |
|  | T-DM1 | 3 |  | 92.56 (P > 0.05) | 7.44 |
| STO#240 | Vehicle | / | Day 83 | 100 | 0 |
|  | MRG002 | 3 |  | 20.70 (P < 0.001) | 79.30 |
|  |  | 10 |  | 18.78 (P < 0.001) | 81.22 |
|  | T-DM1 | 10 |  | 40.96 (P < 0.05) | 59.04 |
| STO#410 | Vehicle | / | Day 38 | 100 | 0 |
|  | MRG002 | 3 |  | 39.94 (P < 0.001) | 60.06 |
|  |  | 10 |  | 0 (P < 0.001) | 100 |
|  | T-DM1 | 10 |  | 108.79 (P > 0.05) | -8.79 |

Notes:
"/" means inapplicable; Tumor Volume (TV) = l × w²/2, where "l" and "w" represents the length and wideth of a tumor, respectively; relative tumor volume (RTV) = $V_f/V_0$, where V0 is the tumor volume measured before grouping (i.e., Day 0) and Vf is the tumor volume measured on the last day of experiment; T/C(%) = (RTV of test article group/RTV of vehicle group) × 100%; TGI % = (average TV of vehicle group − average TV of test article group)/average TV of test article group × 100%.

In vitro cytotoxicity assays showed that MRG002 is markedly more potent than T-DM1 in inhibiting cancer cell growth in a number of breast and gastric cancer cells (Table 7).

In vivo efficacy study results showed that MRG002 significantly inhibited tumor growth in breast and gastric CDX and PDX models and was well tolerated by tumor-bearing mice. Notably, MRG002 significantly inhibited tumor growth in Herceptin®-resistant tumors, and in Kadcyla®-resistant PDX models.

These results demonstrated that MRG002 exhibits improved anti-tumor activity in comparison to currently available ADCs both in vitro and in vivo.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody-drug conjugate comprising:
   an anti-HER2 antibody having greater than about 90% fucosylation,
   at least one molecule of an anti-cancer drug, and
   a linker connecting the anti-HER2 antibody and the at least on molecule of said anti-cancer drug,
   wherein said anti-HER2 antibody is a humanized IgG antibody that comprises a light chain comprising the amino acid sequence set forth in SEQ ID NO:4 and a heavy chain comprising the amino acid sequence set forth in SEQ ID NO:8 or 9,
   wherein the anti-cancer drug is monomethyl auristatin E, and
   wherein the linker comprises a valine citruline dipeptide linker.

2. The antibody-drug conjugate of claim 1, wherein said anti-HER2 antibody has less than about 8% afucosylation.

3. The antibody-drug conjugate of claim 1, wherein said ADC comprises at least three molecules of said anti-cancer drug per molecule of antibody.

4. A composition comprising a plurality of antibody-drug conjugates said antibody-drug conjugates comprising the antibody-drug conjugate of claim 1.

5. The composition of claim 4, wherein said anti-HER2 antibody has less than about 8% afucosylation.

6. The composition of claim 4, wherein said composition comprises a drug/antibody ratio of greater than about 3.5 molecules of said anti-cancer drug per anti-HER2 antibody.

7. The composition of claim 6, wherein said composition comprises a drug/antibody ratio of about 3.6 molecules of said anti-cancer drug per anti-HER2 antibody.

8. A method for treating a mammal having a HER2-expressing cancer, said method comprising:
   administering an effective amount of the antibody-drug conjugate (ADC) of claim 1 to said mammal.

9. The method of claim 8, wherein said mammal is a human.

10. The method of claim 8, wherein said HER2-expressing cancer is a breast cancer or a gastric cancer.

11. The method of claim 8, wherein said HER2-expressing cancer is a refractory cancer.

12. The method of claim 11, wherein said refractory cancer is a trastuzumab resistant cancer or a T-DM1 resistant cancer.

13. The method of claim 8, wherein said anti-HER2 antibody has less than about 8% afucosylation.

14. The method of claim 8, wherein said ADC comprises at least three molecules of the at least one anti-cancer drug per molecule of the anti-HER2 antibody.

15. The method of claim 8, wherein said administering comprising administering about 0.6 mg to about 4 mg of said ADC per kg body weight of said mammal.

16. The method of claim 8, further comprising:
   administering to said mammal one or more additional anti-cancer agents.

17. The method of claim 16, wherein the one or more additional anti-cancer agents comprise an anti-PD-1 antibody.

18. The method of claim 16, wherein the one or more additional anti-cancer agents comprise an anti-PD-L1 antibody.

19. The method of claim 16, wherein the one or more additional anti-cancer agents comprise an anti-CTLA4 antibody.

20. The method of claim 16, wherein the one or more additional anti-cancer agents comprise an anti-TIGIT antibody.

* * * * *